(12) United States Patent
Golovchenko et al.

(10) Patent No.: US 8,394,640 B2
(45) Date of Patent: *Mar. 12, 2013

(54) STUDY OF POLYMER MOLECULES AND CONFORMATIONS WITH A NANOPORE

(75) Inventors: Jene A. Golovchenko, Lexington, MA (US); Jiali Li, Fayetteville, AR (US); Derek Stein, Delft (NL); Marc H. Gershow, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/961,021

(22) Filed: Dec. 6, 2010

(65) Prior Publication Data

US 2011/0159601 A1    Jun. 30, 2011

Related U.S. Application Data

(63) Continuation of application No. 10/918,959, filed on Aug. 16, 2004, now Pat. No. 7,846,738.

(60) Provisional application No. 60/495,292, filed on Aug. 15, 2003.

(51) Int. Cl.
*G01N 33/00* (2006.01)

(52) U.S. Cl. .................. 436/86; 436/94; 436/93; 436/91

(58) Field of Classification Search .................. 436/86, 436/6, 94, 93, 91; 205/778
See application file for complete search history.

(56) References Cited

U.S. PATENT DOCUMENTS

| | | | |
|---|---|---|---|
| 3,815,024 A | 6/1974 | Bean et al. |
| 3,856,633 A | 12/1974 | Fletcher, III |
| 4,456,522 A | 6/1984 | Blackburn |
| 4,521,729 A | 6/1985 | Kiesewetter et al. |
| H201 H | 1/1987 | Yager |
| 4,661,235 A | 4/1987 | Krull et al. |
| 4,874,499 A | 10/1989 | Smith et al. |
| 4,926,114 A | 5/1990 | Doutre |
| 5,001,048 A | 3/1991 | Taylor et al. |
| 5,111,221 A | 5/1992 | Fare et al. |
| 5,221,447 A | 6/1993 | Hjerten |
| 5,234,566 A | 8/1993 | Osman et al. |
| 5,356,776 A | 10/1994 | Kambara et al. |
| 5,376,878 A | 12/1994 | Fisher |
| 5,378,342 A | 1/1995 | Ikematsu et al. |
| 5,503,744 A | 4/1996 | Ikematsu et al. |
| 5,612,179 A | 3/1997 | Simons |
| 5,795,782 A | 8/1998 | Church et al. |
| 5,833,826 A | 11/1998 | Nordman |
| 5,911,871 A | 6/1999 | Preiss et al. |
| 6,015,714 A | 1/2000 | Baldarelli et al. |
| 6,054,035 A | 4/2000 | Kambara |
| 6,156,502 A | 12/2000 | Beattie |
| 6,190,865 B1 | 2/2001 | Jendrisak et al. |
| 6,203,993 B1 | 3/2001 | Shuber et al. |
| 6,210,896 B1 | 4/2001 | Chan |
| 6,214,545 B1 | 4/2001 | Dong et al. |
| 6,221,603 B1 | 4/2001 | Mahtani |
| 6,221,635 B1 | 4/2001 | Rovera et al. |
| 6,238,866 B1 | 5/2001 | Yeh et al. |
| 6,263,286 B1 | 7/2001 | Gilmanshin et al. |
| 6,267,872 B1 | 7/2001 | Akeson et al. |
| 6,355,420 B1 | 3/2002 | Chan |
| 6,362,002 B1 | 3/2002 | Denison |
| 6,403,311 B1 | 6/2002 | Chan |
| 6,428,959 B1 | 8/2002 | Deamer |
| 6,464,842 B1 | 10/2002 | Golovchenko et al. |
| 6,503,409 B1 | 1/2003 | Fleming |
| 6,528,258 B1 | 3/2003 | Russell |
| 6,617,113 B2 | 9/2003 | Deamer |
| 6,627,067 B1 | 9/2003 | Branton et al. |
| 6,673,615 B2 | 1/2004 | Denison et al. |
| 6,746,594 B2 | 6/2004 | Akeson et al. |
| 6,783,643 B2 | 8/2004 | Golovchenko et al. |
| 7,189,503 B2 | 3/2007 | Akeson et al. |
| 7,238,485 B2 | 7/2007 | Akeson et al. |
| 7,468,271 B2 | 12/2008 | Golovchenko et al. |
| 7,625,706 B2 | 12/2009 | Akeson et al. |
| 7,846,738 B2 | 12/2010 | Golovchenko et al. |
| 7,947,454 B2 | 5/2011 | Akeson et al. |
| 2002/0039737 A1 | 4/2002 | Chan et al. |
| 2002/0081744 A1 | 6/2002 | Chan et al. |
| 2002/0119455 A1 | 8/2002 | Chan et al. |
| 2003/0044816 A1 | 3/2003 | Denison et al. |
| 2003/0059822 A1 | 3/2003 | Chan et al. |
| 2003/0066749 A1 | 4/2003 | Golovchenko et al. |
| 2003/0104428 A1 | 6/2003 | Branton et al. |

(Continued)

FOREIGN PATENT DOCUMENTS

| | | |
|---|---|---|
| DE | 30 28 569 A1 | 2/1982 |
| EP | 1 009 802 B1 | 8/2004 |

(Continued)

OTHER PUBLICATIONS

Meller, Amit et al., Rapid nanopore discrimination between single polynucleotide molecules, PNAS, Feb. 1, 2000, vol. 97, No. 3, 1079-1084.*

Dreamer, David W. Characterization of Nucleic Acids by Nanopore Analysis, Acc. Chem. Res., 2002, 95, 917-925.*

Akeson et al., "Microsecond Time-Scale Discrimination among Polycytidylic Acid, Polyadenylic Acid, and Polyuridylic Acid as Homopolymers or as Segments within Single RNA Molecules," *Biophys. J.* 77:3227-3233 (1999).

Auld et al., "A Neutral Amino Acid Change in Segment IIS4 Dramatically Alters the Gating Properties of the Voltage-Dependent Sodium Channel," *Proc. Natl. Acad. Sci. USA* 87:323-327 (1990).

Andersen, "Sequencing and the Single Channel," *Biophys. J.* 77:2899-2901 (1999).

(Continued)

*Primary Examiner* — Christine T Mui
(74) *Attorney, Agent, or Firm* — Clark + Elbing LLP; Kristina Bieker-Brady

(57) ABSTRACT

The invention features methods for evaluating the conformation of a polymer, for example, for determining the conformational distribution of a plurality of polymers and to detect binding or denaturation events. The methods employ a nanopore which the polymer, e.g., a nucleic acid, traverses. As the polymer traverses the nanopore, measurements of transport properties of the nanopore yield data on the conformation of the polymer.

30 Claims, 8 Drawing Sheets

U.S. PATENT DOCUMENTS

| | | |
|---|---|---|
| 2004/0110205 A1 | 6/2004 | Wang |
| 2005/0053961 A1 | 3/2005 | Akeson et al. |
| 2005/0241933 A1 | 11/2005 | Branton et al. |
| 2006/0057585 A1 | 3/2006 | McAllister |
| 2006/0063171 A1 | 3/2006 | Akeson et al. |
| 2007/0054276 A1 | 3/2007 | Sampson |
| 2007/0190542 A1 | 8/2007 | Ling et al. |
| 2007/0194225 A1 | 8/2007 | Zorn |
| 2007/0281329 A1 | 12/2007 | Akeson et al. |
| 2008/0102504 A1 | 5/2008 | Akeson et al. |
| 2010/0028681 A1 | 2/2010 | Dai et al. |
| 2011/0159601 A1 | 6/2011 | Golovchenko et al. |
| 2012/0094278 A1 | 4/2012 | Akeson et al. |

FOREIGN PATENT DOCUMENTS

| | | |
|---|---|---|
| EP | 1 038 171 B1 | 2/2006 |
| GB | 2 232 769 A | 12/1990 |
| WO | WO 94/25862 A1 | 11/1994 |
| WO | WO 98/35012 A2 | 8/1998 |
| WO | WO 99/24823 A1 | 5/1999 |
| WO | WO 00/09757 A1 | 2/2000 |
| WO | WO 00/56937 A2 | 9/2000 |
| WO | WO 00/78668 A1 | 12/2000 |
| WO | WO 00/79257 A1 | 12/2000 |
| WO | WO 01/18251 A1 | 3/2001 |
| WO | WO 01/42782 A1 | 6/2001 |
| WO | WO 01/59684 A2 | 8/2001 |
| WO | WO 02/42496 A2 | 5/2002 |
| WO | WO 03/000920 A2 | 1/2003 |
| WO | WO 03/003446 A2 | 1/2003 |
| WO | WO 2004/077503 | 9/2004 |
| WO | WO 2009/046094 | 4/2009 |
| WO | WO 2010/138136 | 12/2010 |

OTHER PUBLICATIONS

Bayley et al., "Stochastic Sensors Inspired by Biology," *Nature* 413:226-230 (2001).
Bensimon et al., "Alignment and Sensitive Detection of DNA by a Moving Interface," *Science* 265:2096-2098 (1994).
Benz et al., "Pore Formation by LamB of *Escherichia coli* in Lipid Bilayer Membranes," *J. Bacteriol.* 165:978-986 (1986).
Bezrukov et al., "Counting Polymers Moving through a Single Ion Channel," *Nature* 370:279-281 (1994).
Boulain et al., "Mutagenesis by Random Linker Insertion into the LamB Gene of *Escherichia coli* K12," *Mol. Gen. Genet.* 205:339-348 (1986).
Boulanger et al., "Characterization of Ion Channels Involved in the Penetration of Phage T4 DNA into *Escherichia coli* Cells," *J. Biol. Chem.* 263:9767-9775 (1988).
Boulanger et al., "Ion Channels are Likely to be Involved in the Two Steps of Phage T5 DNA Penetration into *Escherichia coli* Cells," *J. Biol. Chem.* 267:3168-3172 (1992).
Boyd et al., "Determinants of Membrane Protein Topology," *Proc. Natl. Acad. Sci. USA* 84:8525-8529 (1987).
Branton et al., "Biochemical Sensors. Adapting to Nanoscale Events," *Nature* 398:660-661 (1999).
Branton et al., "Adapting to Nanoscale Events," *Nature* 398:660-661, 1999.
Branton et al., "The Potential and Challenges of Nanopore Sequencing," *Nat. Biotechnol.* 26:1146-1153 (2008).
Charbit et al., "Probing the Topology of a Bacterial Membrane Protein by Genetic Insertion of a Foreign Epitope; Expression at the Cell Surface," *EMBO J.* 5:3029-3037 (1986).
Charbit et al., "Permissive Sites and Topology of an Outer Membrane Protein with a Reporter Epitope," *J. Bacteriol.* 173:262-275 (1991).
Dargent et al., "Effect of Point Mutations on the In-Vitro Pore Properties of Maltoporin, a Protein of *Escherichia coli* Outer Membrane," *J. Mol. Biol.* 201:497-506 (1988).
Dargent et al., "Selectivity for Maltose and Maltodextrins of Maltoporin, a Pore-Forming Protein of *E. coli* Outer Membrane," *FEBS Lett.* 220:136-142 (1987).
Deamer et al., "Nanopores and Nucleic Acids: Prospects for Ultrarapid Sequencing," *Trends Biotechnol.* 18:147-151 (2000).

DeBlois et al., "Sizes and Concentrations of Several Type C Oncornaviruses and Bacteriophage T2 by the Resistive-Pulse Technique," *J. Virol.* 23:227-233 (1977).
DeBlois et al., "Electrokinetic Measurements with Submicron Particles and Pores by the Resistive Pulse Technique," *J. Colloid Interface Sci.* 61:323-335 (1977).
Ehrmann et al., "Genetic Analysis of Membrane Protein Topology by a Sandwich Gene Fusion Approach," *Proc. Natl. Acad. Sci. USA* 87:7574-7578 (1990).
Ferenci et al., "Channel Architecture in Maltoporin: Dominance Studies with LamB Mutations Influencing Maltodextrin Binding Provide Evidence for Independent Selectivity Filters in Each Subunit," *J. Bacteriol.* 171:855-861 (1989).
Fologea et al., "DNA Conformation and Base Number Simultaneously Determined in a Nanopore," *Electrophoresis* 28:3186-3192 (2007). Fologea et al., "DNA Conformation and Base Number Simultaneously Determined in a Nanopore," *Electrophoresis* 28:3186-3192 (2007).
Ghadiri et al., "Artificial Transmembrane Ion Channels from Self-Assembling Peptide Nanotubes," *Nature* 369:301-304 (1994).
Hall et al., "Alamethicin. A Rich Model for Channel Behavior," *Biophys. J.* 45:233-247 (1984).
Hamill et al., "Improved Patch-Clamp Techniques for High-Resolution Current Recording from Cells and Cell-Free Membrane Patches," *Pflügers Arch.* 391:85-100 (1981).
Harrington et al.,"The F Pilus of *Escherichia coli* Appears to Support Stable DNA Transfer in the Absence of Wall-to-Wall Contact between Cells," *J. Bacteriol.* 172:7263-7264 (1990).
Heinemann et al., "Open Channel Noise: IV. Estimation of Rapid Kinetics of Formamide Block in Gramicidin A Channels," *Biophys. J.* 54:757-764 (1988).
Heinemann et al., "Open Channel Noise: V. Fluctuating Barriers to Ion Entry in Gramicidin A Channels," *Biophys. J.* 57:499-514 (1990).
Henry et al., "Blockade of a Mitochondrial Cationic Channel by an Addressing Peptide: An Electrophysiological Study," *J. Membr. Biol.* 112:139-147 (1989).
Hornblower et al., "Single-Molecule Analysis of DNA-Protein Complexes Using Nanopores," *Nat. Methods* 4:315-317 (2007) (including Supplementary Materials, pp. 1-6).
Hoshi et al., "Biophysical and Molecular Mechanisms of Shaker Potassium Channel Inactivation," *Science* 250:533-538 (1990).
Hoshi et al., "Two Types of Inactivation in Shaker $K^+$ Channels: Effects of Alterations in the Carboxy-Terminal Region," *Neuron* 7:547-556 (1991).
Howorka et al., "Sequence-Specific Detection of Individual DNA Strands Using Engineered Nanopores," *Nat. Biotechnol.* 19:636-639 (2001).
Kasianowicz et al., "Characterization of Individual Polynucleotide Molecules Using a Membrane Channel," *Proc. Natl. Acad. Sci. USA* 93:13770-13773 (1996).
Kubitschek, "Electronic Counting and Sizing of Bacteria," *Nature* 182:234-235 (1958).
Lakey et al., "The Voltage-Dependent Activity of *Escherichia coli* Porins in Different Planar Bilayer Reconstitutions," *Eur. J. Biochem.* 186:303-308 (1989).
Lopez et al., "Hydrophobic Substitution Mutations in the S4 Sequence Alter Voltage-Dependent Gating in Shaker $K^+$ Channels," *Neuron* 7:327-336 (1991).
Li et al., "DNA Molecules and Configurations in a Solid-State Nanopore Microscope," *Nat. Mater.* 2:611-615 (2003).
Li et al., "Ion-Beam Sculpting at Nanometre Length Scales," *Nature* 412:166-169 (2001).
Marquis et al., "SpoIIIE Strips Proteins Off the DNA During Chromosome Translocation," *Genes Dev.* 22:1786-1795 (2008).
Meller and Branton, "Single Molecule Measurements of DNA Transport through a Nanopore," *Electrophoresis* 23:2583-2591 (2002).
Meller et al., "Voltage-Driven DNA Translocations through a Nanopore," *Phys. Rev. Lett.* 86:3435-3438 (2001).
Moellerfeld et al., "Improved Stability of Black Lipid Membranes by Coating with Polysaccharide Derivatives Bearing Hydrophobic Anchor Groups," *Biochem. Biophys. Acta.* 857:265-270 (1986).

Movileanu et al., "Detecting Protein Analytes that Modulate Transmembrane Movement of a Polymer Chain within a Single Protein Pore," *Nat. Biotechnol.* 18:1091-1095 (2000).

Nauck et al., "Detection of Mutations in the Apolipoprotein CII Gene by Denaturing Gradient Gel Electrophoresis. Identification of the Splice Site Variant Apolipoprotein CII-Hamburg in a Patient with Severe Hypertriglyceridemia," *Clin. Chem.* 44:1388-1396 (1998).

Nath et al., "Transcription by T7 RNA Polymerase Using Benzo[a]pyrene-Modified Templates," Carcinogenesis 12:973-976 (1991).

Neher et al., "Single-Channel Currents Recorded from Membrane of Denervated Frog Muscle Fibers," *Nature* 260:799-802 (1976).

Novick et al., "Fluorescence Measurement of the Kinetics of DNA Injection by Bacteriophage λ into Liposomes," *Biochemistry* 27:7919-7924 (1988).

Ohba et al., "Induction of DNA Replication by Transcription in the Region Upstream of the Human c-myc Gene in a Model Replication System," *Mol. Cell. Biol.* 16:5754-5763 (1996).

Ollis et al., "Domain of *E. coli* DNA Polymerase I Showing Sequence Homology to T7 DNA Polymerase," *Nature* 313:818-819 (1985).

Ollis et al., "Structure of Large Fragment of *Escherichia coli* DNA Polymerase I Complexed with dTMP," *Nature* 313:762-766 (1985).

Ovchinnikov et al., "3. The Cyclic Peptides: Structure, Conformation, and Function: P. Gramicidin S. (851) Its Analogs and Tyrocidines A-C (904-906)," The Proteins, Third Edition 5:547-555 (1982).

Ovchinnikov et al., "3. The Cyclic Peptides: Structure, Conformation, and Function: T. Valinomycin (913)," The Proteins, Third Edition 5:563-573 (1982).

Patton et al., "Amino Acid Residues Required for Fast $Na^+$-Channel Inactivation: Charge Neutralizations and Deletions in the III-IV Linker," *Proc. Natl. Acad. Sci. USA* 89:10905-10909 (1992).

Sauer-Budge et al., "Unzipping Kinetics of Double-Stranded DNA in a Nanopore," *Phys. Rev. Lett.* 90:238101 (2003).

Shiver et al., "On the Explanation of the Acidic pH Requirement for In Vitro Activity of Colicin E1. Site-Directed Mutagenesis at Glu-468," *J. Biol. Chem.* 262:14273-14281 (1987).

Sigworth et al., "Open Channel Noise. III. High-Resolution Recordings Show Rapid Current Fluctuations in Gramicidin A and Four Chemical Analogues," *Biophys. J.* 52:1055-1064 (1987).

Simon et al., "A Protein-Conducting Channel in the Endoplasmic Reticulum," *Cell* 65:371-380 (1991).

Smith et al., "Images of a Lipid Bilayer at Molecular Resolution by Scanning Tunneling Microscopy," *Proc. Natl Acad. Sci. U S A* 83:969-972 (1987).

Sukharev et al., "Electroporation and Electrophoretic DNA Transfer into Cells: The Effect of DNA Interaction with Electropores," *Biophys. J.* 63:1320-1327 (1992).

Taylor et al., "'Reversed' Alamethicin Conductance in Lipid Bilayers," *Biophys. J.* 59:873-879 (1991).

Titov et al., "Sandwiched Graphene-Membrane Superstructures," *ACS Nano*, 4:229-234 (2010).

Vercoutere et al., "Rapid Discrimination among Individual DNA Hairpin Molecules at Single-Nucleotide Resolution Using an Ion Channel," *Nat. Biotechnol.* 19:248-252 (2001).

Wang et al., "Nanopores with a Spark for Single-Molecule Detection," *Nat. Biotechnol.* 19:622-623 (2001).

Weiss et al., "Molecular Architecture and Electrostatic Properties of a Bacterial Porin," *Science* 254:1627-1630 (1991).

West et al., "A Cluster of Hydrophobic Amino Acid Residues Required for Fast $Na^+$-Channel Inactivation," *Proc. Natl. Acad. Sci. USA* 89:10910-10914 (1992).

White et al., "Single Ion-Channel Recordings Using Glass Nanopore Membranes," *J. Am. Chem. Soc.* 129:11766-11775 (2007).

Whatman™ Ltd., "Nytran Nylon membranes," product description (available at http://www.whatman.com/NytranNylonMembranes.aspx, accessed Jan. 29, 2009).

Wonderlin et al., "Optimizing Planar Lipid Bilayer Single-Channel Recordings for High Resolution with Rapid Voltage Steps," *Biophys. J.* 58:289-297 (1990).

Wu et al., "*Bacillus subtilis* SpoIIIE Protein Required for DNA Segregation During Asymmetric Cell Division," *Science* 264:572-575 (1994).

Zavriev et al., "RNA Polymerase-Dependent Mechanism for the Stepwise T7 Phage DNA Transport from the Virion into *E. coli*," *Nucleic Acids Res.* 10:1635-1652 (1982).

Benz et al., "Mechanism of Sugar Transport through the Sugar-Specific LamB Channel of *Escherichia coli* Outer Membrane," *J. Membr. Biol.* 100:21-29 (1987).

Beckmann et al. "Alignment of Conduits for the Nascent Polypeptide chain in the Ribosome-Sec61 Complex" 278:2123 (1997).

* cited by examiner

STUDY OF POLYMER MOLECULES AND CONFORMATIONS WITH A NANOPORE

CROSS-REFERENCE TO RELATED APPLICATIONS

This application is a continuation of U.S. application Ser. No. 10/918,959, filed Aug. 16, 2004, now U.S. Pat. No. 7,846,738, and claims benefit of U.S. Provisional Application No. 60/495,292, filed on Aug. 15, 2003, each of which is hereby incorporated by reference.

STATEMENT AS TO FEDERALLY SPONSORED RESEARCH

The invention was made with U.S. Government support under Grant No. 0073590 awarded by the National Science Foundation, Grant No. F49620-01-1-0467 awarded by the Air Force Research Laboratory, and Grant No. DE-FG02-01ER45922 awarded by the Department of Energy. The Government has certain rights in this invention.

BACKGROUND OF THE INVENTION

The invention relates to the field polymer characterization.

Probing, characterizing, and manipulating single polymers like DNA is often accomplished with the aid of optical methods, e.g., observing evanescent field fluorescence of dye molecules, deflecting light beams in atomic force microscopes, or trapping attached dielectric objects with optical tweezers. There has also been remarkable progress at the molecular level in the study of the electrical ionic conduction signals from voltage biased nanoscale biopores. More recently, a voltage bias on an alpha hemolysin biopore has been shown to induce charged single-stranded DNA and RNA molecules to translocate through the pore. Each translocating molecule blocks the open pore ionic current providing an electrical signal that depends on several characteristics of the molecule. This system has limits for studies of biological molecules: the pore is of a fixed size, and its stability and noise characteristics are restricted by chemical, mechanical, electrical, and thermal constraints.

Thus, there is a need for new apparatus and methods for studying polymer molecules.

SUMMARY OF THE INVENTION

The invention features methods for evaluating the conformation of a polymer, for example, for determining the conformational distribution of a plurality of polymers and to detect binding or denaturation events. The methods employ a nanopore which the polymer, e.g., a nucleic acid, traverses. As the polymer traverses the nanopore, measurements of transport properties of the nanopore yield data on the conformation of the polymer.

In one aspect, the invention features a method for determining the conformation of a polymer, including providing an apparatus having a membrane with a nanopore; first and second fluid reservoirs separated by the membrane and fluidically connected via the nanopore; and a detector capable of detecting time-dependent changes in transport properties of the nanopore; placing the polymer in the first reservoir; causing the polymer to traverse the nanopore from the first to the second reservoir; and measuring the transport properties of the nanopore over time, wherein changes in the transport properties over time are indicative of the conformation of the polymer. An intervention, as described herein, may also be applied prior to causing the polymer to traverse the nanopore.

The invention further features a method for evaluating the effects of an intervention on the conformation of a polymer, including the steps of providing an apparatus as described above; providing transport properties of the nanopore over time of the polymer in the absence of the intervention, wherein changes in the transport properties over time are indicative of the conformation of the polymer in the absence of the intervention; placing the polymer in the first reservoir; applying the intervention; causing the polymer to traverse the nanopore from the first to the second reservoir; measuring the transport properties of the nanopore over time, wherein changes in the transport properties over time are indicative of the conformation of the polymer in the presence of the intervention; comparing the transport properties of the nanopore over time with and without the intervention, wherein the difference between the transport properties is indicative of the effect of the intervention on the conformation of the polymer. The intervention may or may not include a chemical species, e.g., a candidate binding compound, a denaturant, or a nucleic acid. Exemplary non-chemical interventions include a temperature change, light, voltage, or magnetic fields. This method may also be employed to determine changes in conformation caused by altering an existing intervention, without the need for comparison to the conformation of the polymer in the total absence of a particular intervention.

In various embodiments, the polymer is a nucleic acid (e.g., single-or double-stranded DNA or RNA), a protein, a synthetic polymer, or a polysaccharide. The transport property is for example, current, conductance, resistance, capacitance, charge, concentration, an optical property, or chemical structure. The membrane may be a solid state membrane. The nanopore may also include a biological pore. The longitudinal and transverse dimensions of the nanopore may independently range from 1-1000 nm. The polymer may be induced to traverse the nanopore by employing diffusion, electrophoresis, electroosmosic flow, hydrodynamic pressure, magnetic force, optical trapping, mechanical force, or a molecular motor. The methods of the invention may be repeated on the same polymer, e.g., wherein in the repetition a nanopore of different transverse dimension is employed or wherein a different type (e.g., change in chemical species, change in non-chemical intervention, or change from chemical to non-chemical intervention, or vice versa) or extent (e.g., change in concentration of chemical species or change in temperature or amount of non-chemical intervention employed) of intervention is employed.

By "conformation" is meant any non-primary structure of a polymer, including secondary, tertiary, and quaternary structure. A conformation may be thermally stable or unstable under the experimental conditions used. Quaternary structure include any specific or non-specific binding interactions between a polymer and one or more additional chemical species.

By "polymer" is meant any molecule consisting of two or more monomers and capable of having non-primary structure. Monomers may or may not be chemically identical. For the purposes of this invention, the term may encompass an aggregate of a polymer and one or more additional chemical species.

By "transport properties of said nanopore" is meant property measurable during polymer traversal of the nanopore. The transport property may be a function of the solvent, the polymer, a label on the polymer, other solutes (e.g., ions), or an interaction between the nanopore and the solvent or polymer.

DETAILED DESCRIPTION OF THE INVENTION

Figure 1:
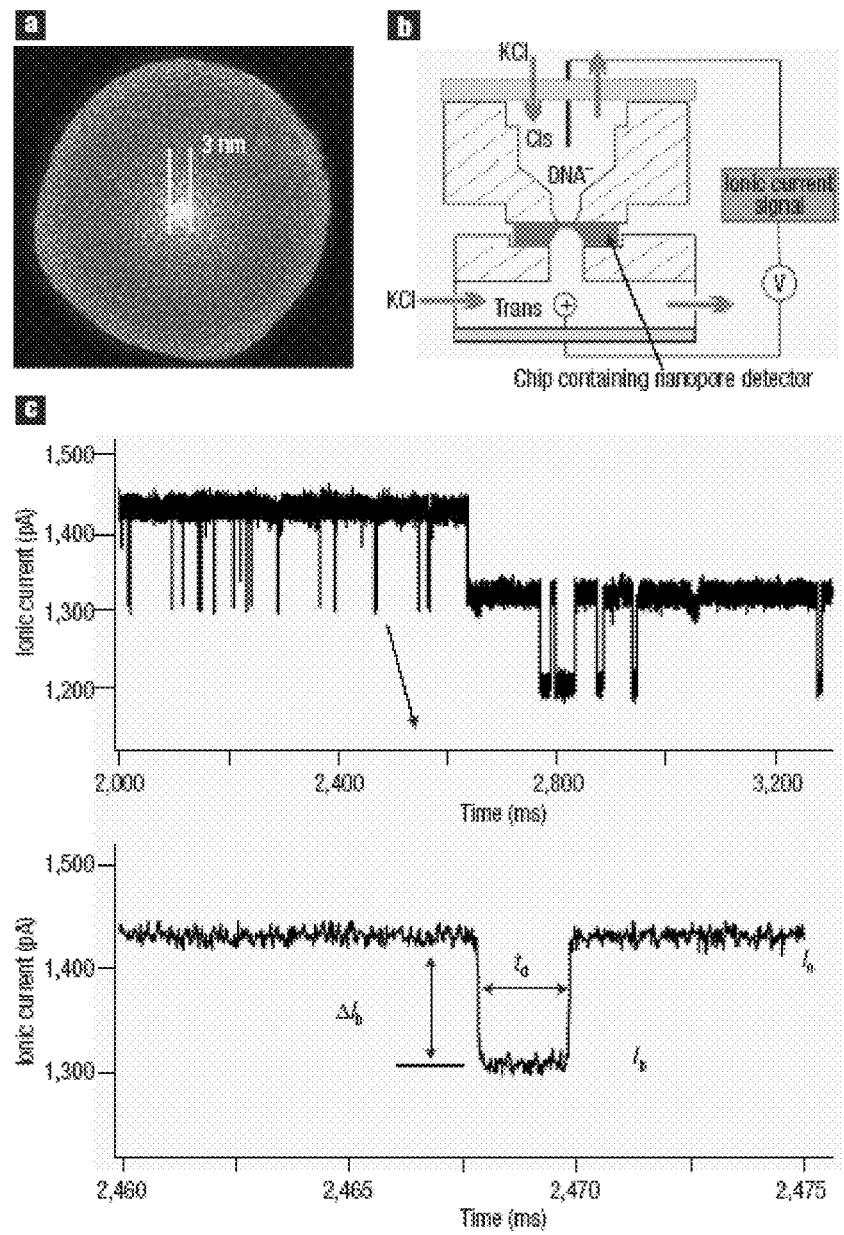
FIG. 1. Details of the experimental setup. a) TEM image of a ~3 nm silicon nitride nanopore. b) Schematic of the apparatus used to obtain electrical signals from single DNA molecules. c) Characteristic signals showing transient molecular current blockades and a baseline current shift. Parameters $t_d$ and $<\Delta I_b>$ are shown for a selected simple molecular event.

A nanometer scale pore, e.g., in a solid-state membrane, enables a technique in accordance with the invention to probe the structure of single polymers, including those of biological interest in their native environments. Previous work with biological protein pores wide enough to pass and sense single stranded DNA molecules demonstrates the power of the nanopore approach to detect linear sequence information and hybridization events, but many future tasks and applications call for a robust solid-state pore whose nanometer scale dimensions and properties may be selected, as one selects the lenses of a microscope.

Methods

The method of the invention observes individual molecules, e.g., of double stranded DNA, and their conformations, e.g., folding behavior, binding, pairing, and hybridization, as they traverse the nanopore. The nanopore may be described as having longitudinal and transverse dimensions. The longitudinal dimensions of the nanopore determine the distance that a polymer must travel to pass through the pore, i.e., the thickness of the pore. The transverse dimensions of the nanopore determine the largest species that can enter the pore, i.e., the width of the pore. Desirably, the longitudinal dimension of the nanopore is small enough to restrict the polymer to a discrete set of measurable conformations. The longitudinal dimension is also desirably smaller than the conformation being observed. Nanopores useful in the invention typically range in transverse dimension from 1-1000 nm, e.g., at most 750, 500, 400, 300, 250, 200, 150, 100, 90, 80, 70, 60 50, 40, 30, 20, 10, 9, 8, 7, 6, 5, 4, 3, or 2 nm and at least 2, 3, 4, 5, 6, 7, 8, 9, 10, 20, 30, 40, 50, 60, 70, 80, 90, 100, 150, 200, 250, 300, 400, 500, or 750 nm. Nanopores useful in the invention typically range in longitudinal dimension from 1-1000 nm, e.g., at most 750, 500, 400, 300, 250, 200, 150, 100, 90, 80, 70, 60 50, 40, 30, 20, 10, 9, 8, 7, 6, 5, 4, 3, or 2 nm and at least 2, 3, 4, 5, 6, 7, 8, 9, 10, 20, 30, 40, 50, 60, 70, 80, 90, 100, 150, 200, 250, 300, 400, 500, or 750 nm. The dimensions of the nanopore employed will depend on the type of polymer being probed and the conditions of the polymer solution.

Individual polymer molecules may be induced to traverse the aperture by a variety of mechanisms, e.g., diffusion, electrophoretic force for charged polymers, electroosmotic flow, hydrodynamic pressure, magnetic force for polymers labeled with a magnetic moiety, optical trapping, mechanical force (e.g., from an atomic force microscope), and molecular motors, e.g., ribosomes or enzymes such as exonucleases, polymerases, and helicases. This method enables alternative probing mechanisms and applications including the study of molecular structure, e.g., conformation, and sequencing. As the polymer is traversing the pore, transport properties of the carrying fluid or the polymer itself are monitoring to determine the conformation of the polymer. Exemplary transport properties include current, conductance, resistance, capacitance, charge, concentration, optical properties (e.g., fluorescence and Raman scattering), and chemical structure.

The methods may be used to study any polymer whose movement through a suitably sized pore can be monitored. Polymers may be naturally occurring or synthetic. Exemplary polymers include nucleic acids (e.g., DNA and RNA), proteins, polysaccharides, lipids, and synthetic polymers.

A typical apparatus of the invention includes a voltage-biased nanopore, fabricated in a suitable configuration, e.g., a silicon nitride membrane. Alternative methods of inducing polymer traversal through the nanopore are described herein. In this embodiment, the membrane separates two chambers of conducting electrolyte solution. The only electrical conduction path from one chamber to the other passes through the nanopore. For double stranded DNA (ds DNA), transverse and longitudinal dimensions of the pore are smaller than the molecule persistence length, 50 nm for ds DNA, and the transverse dimension of the pore is larger than the ~2 nm cross sectional size of the molecule. In one example, a nanopore having a transverse dimension of 10 nm of the invention offers the new ability to observe folding in DNA. Smaller pores, e.g., solid-state nanopore and hemolysin pores having a transverse dimension of 3 nm, do not allow the passage of a folded ds DNA molecule, while other constrictions recently demonstrated are much larger than the persistence length of ds DNA and so do not restrict the passage of DNA to a discrete set of measurable conformations. A schematic of a typical experimental setup is shown in FIG. 1b.

The solid state nanopore microscope and method of the invention enables an interpretation of the time histories of individual molecules—and their structures—as they pass through the nanopore, in terms of the corresponding highly modulated individual events. The nanopore apparatus and method of the invention thereby enables the resolution of multiple features on a single molecule without a priori knowledge of the feature's characteristics, and to observe new phenomena, like molecular folding, binding, hybridization, and pairing, by means that have not been available in narrower existing biological pores. This significantly augments previous work showing that biological pores can distinguish between molecules whose chemical structures provide selective binding to a biological pore, and work that shows biological pores can trap and sense the spontaneous disassociation of carefully prepared DNA hairpins that are frustrated from translocating the biological pore in their associated form. The solid state pores of the invention provide a new way to study the conformations, e.g., folding, binding, hybridization, and pairing configurations, of single long chain molecules, the differences between chemically identical molecules in a statistical ensemble, and induced changes in molecular structure that, because of energy restrictions, do not occur typically in solution.

A further advantage of solid-state pores is the ability it provides for articulating the nanopores with electrically conducting electrodes. Such electrodes can allow electronic tunneling and near field optical studies of translocating molecules that are confined in a nanopore. Applying these new physical local interactions to molecules translocating through nanopores can provide local single molecule spectroscopies not afforded by measurement of ionic current alone and offer a means of increasing longitudinal resolution, possibly to the single-base level for DNA, allowing for extremely rapid sequencing of long molecules.

The ability to determine the conformation of polymers in solution has several uses. For example, the methods of the invention may be used to survey a plurality of polymers in a solution to determine the conformational distribution of the population. In addition, conformational changes caused by an intervention can be studied. For example, a chemical species, e.g., drugs, ions, oliogomers, surfactants, nucleotide probes and primers, cofactors, enzyme substrates, and other polymers, may be added to the solution containing the polymer being studied, and a change in conformation can be used to monitor the effects of the species on the polymer, e.g., binding, hybridization, pairing, denaturation, stabilizing a particular conformation, or other induced conformation change. Such studies may be employed for drug discovery (e.g., by assaying for candidate binding compounds) and proteomics. Non-chemical interventions, e.g., a temperature change, magnetic field, light, or voltage, may also be employed to determine the effects on conformation. In addition, as the method monitors the conformation as the polymer traverses an aperture, the relative, or absolute, location of conformation may be ascertained, e.g., to determine the location of a conformation or changes in conformation or to determine the location of binding of a chemical species, e.g., as in probe or primer hybridization to a nucleic acid. The methods may also be used to monitor the chemical makeup or purity of a population of polymers, e.g., the concentration of a desired polymer or the chemical structure of a polymer, e.g., branched or linear. The methods of the invention may also be repeated using, for example, nanopores of different sizes to further probe one or more polymers.

Detection

Time-dependent transport properties of the aperture may be measured by any suitable technique. The transport properties may be a function of the liquid used to transport the polymer, solutes (e.g., ions) in the liquid, the polymer (e.g., chemical structure of the monomers), or labels on the polymer. Exemplary transport properties include current, conductance, resistance, capacitance, charge, concentration, optical properties (e.g., fluorescence and Raman scattering), and chemical structure.

Desirably, the transport property is current. Suitable methods for detecting current in nanopore systems are known in the art, for example, as described in U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428. In another embodiment, the transport property is electron flow across the aperture, which may be monitored by electrodes disposed adjacent the nanopore.

Fabrication of Nanopores

Any nanopore of the appropriate size may be used in the methods of the invention. Nanopores may be biological, e.g., proteinaceous, or solid-state. Suitable nanopores are described, for example, in U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428. Solid-state nanopores can be fabricated with arbitrary size apertures, enabling the study of single molecules in a vast category of polymers in solution, including RNA, hybridized DNA, proteins, and synthetic polymers. An apparatus based on a solid-state nanopore in accordance with the invention provides distinct differences and advantages over extant biopore detectors. For example, for ds DNA molecules whose transverse size is ~2 nm, a hemolysin biopore cannot translocate such a large diameter molecule. Furthermore, because of their physical robustness, solid-state nanopores may well be used to study molecules at extremes of temperature, voltage, and pH conditions that would destroy biopore-membrane systems.

An exemplary method for fabricating solid-state membranes is the ion beam sculpting method described in Li et al. Nature 2001, 412:166. The ion beam sculpting process as described herein allows structures to be fabricated with desired nanometer scale dimensions from solid state materials like silicon nitride. Solid-state encompasses both organic and inorganic materials including, but not limited to, microelectronic materials, insulating materials such as $Si_3N_4$, $Al_2O_3$, and SiO, organic and inorganic polymers such as polyamide, plastics such as polytetrafluoroethylene, or elastomers such as two-component addition-cure silicone rubber, and glasses, although there is no specific limitation to the materials that may be used according to the invention.

The manipulation of matter at the nanometer scale is important for many electronic, chemical, and biological advances, but conventional solid state fabrication methods do not typically reproducibly achieve $10^{-9}$ meter dimensional control. The ion beam sculpting process overcomes the limitations of conventional fabrication processes to provide a method for precisely controlling nanoscale feature fabrication, specifically with the use of low energy ion beams. Ion beam sculpting control in accordance with the invention is found to reveal surprising atomic transport phenomena that occur in a variety of materials and geometries, leading to discoveries of control techniques.

Ion beam sculpting in accordance with the invention can be employed for fabricating a wide range of nanoscale features, including, e.g., molecular scale holes and apertures, or nanopores, in a solid state material, e.g., a thin solid state membrane. Nanopores can serve to localize molecular scale electrical junctions and switches and function as masks to create other small scale structures. Solid state nanopores can also function in a manner analogous to membrane channels in living systems, serving as extremely sensitive electromechanical devices for regulating electrical potential, ionic flow, and molecular transport across a membrane. In accordance with the invention, controlled ion-beam sculpting has been experimentally employed to produce a robust electronic detector consisting of a single nanopore in a $Si_3N_4$ membrane, capable of registering single DNA molecules in aqueous solution.

Figure 6:
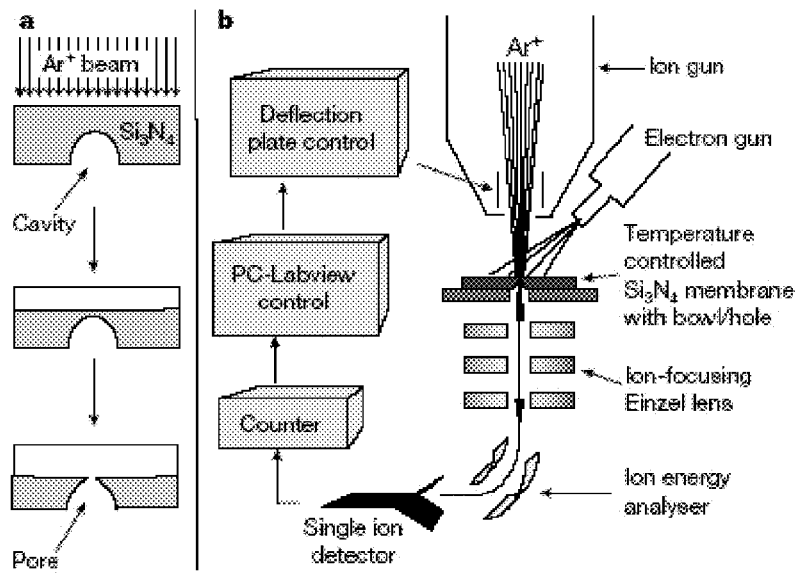
FIG. 6. Strategy to make nanopores using argon ion-beam sputtering. a) Sputtering removes material from a free-standing $Si_3N_4$ membrane with a cavity. b) Feedback controlled ion-beam sculpting apparatus housed in a high-vacuum chamber. a) A 500-nm-thick low-stress (~200 MPa tensile) $Si_3N_4$ film was deposited on a (100) silicon substrate by low-pressure chemical vapor deposition. Photolithography and directional wet chemical etching of silicon were used to create a free-standing 25 μm×25 μm $Si_3N_4$ membrane. Either a bowl-shaped cavity (a), or a single initial pore of ~0.1 μm diameter (not shown), was created near the center of the membrane using, respectively, reactive ion etching or a focused ion beam (FIB) machine. b) A differentially pumped ion gun (VG Microtech model EX05) exposes the sample surface to an $Ar^+$ beam, ~0.2 μm in diameter. A Channeltron (Gallileo Optics) electron-multiplier style single-ion detector, positioned after the sample, counts transmitted ions. Detection plates at the exit port of the ion gun could detect the beam off the sample or pulse the ion beam on and off the sample. A focusing Einzel lens and 60° electrostatic detection system between sample and detector are used to suppress electron, ion and X-ray backgrounds. A 50-eV electron gun (Kimball Physics Model FRA-2x1-1) floods the sample to neutralize surface charging. A liquid-nitrogen-cooled shroud surrounds the sample and Einzel lens and a quadrupole mass spectrometer, connected to the $10^{-9}$ torr turbo-pumped vacuum chamber, monitors residual gas composition. A thermocouple monitors the sample holder temperature, which is adjusted with cold nitrogen gas and a resistance heater.

When ions are directed to a material surface from an ion beam, a number of processes are understood to occur. In one such process, a sputtering process, atomic-scale erosion occurs at the material surface, removing approximately one atom from the surface for every incident ion. Because of this phenomena, as material is removed from a solid state surface, e.g., a $Si_3N_4$ surface, which has been processed to contain a bowl-shaped cavity on its opposite surface, as shown in FIG. 6a, top, the flat surface will ultimately intercept the bottom of the bowl shaped cavity, forming a nanopore, as shown in FIG. 6a, bottom. Production of a nanopore in this manner requires knowledge of precisely when to stop the ion sputtering erosion process. The apparatus shown in FIG. 6b implements a feedback-controlled ion sputtering system that counts the ions transmitted through the opening pore and extinguishes the erosion process at an appropriate time corresponding to a desired pore size. It is preferred that the apparatus also be operated to control a number of processing parameters found to be important to the ion beam sculpting process, including sample temperature; ion beam duty cycle, defined as the time the beam is on, divided by the sum of the times the beam is on and off, for a pulsed beam; and the instantaneous ion beam flux, F, in ions $nm^{-2}s^{-1}$ when the beam is directed to the eroding material.

Figure 7:
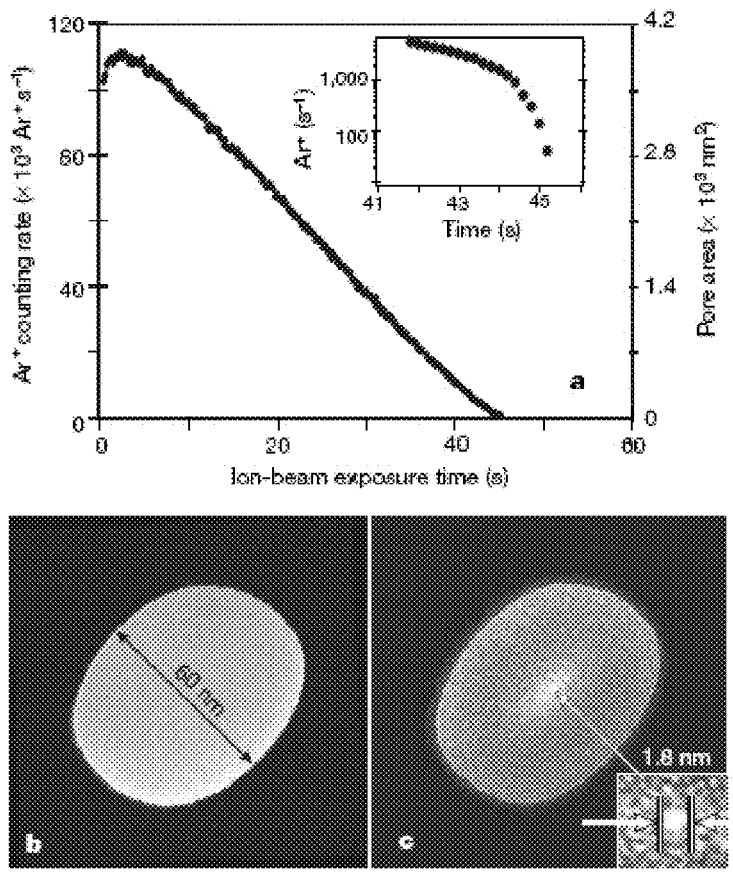
FIG. 7. Sculpting a nanopore. a) Transmitted ion count rate (left axis) and pore area (right axis) versus integrated time the ion beam is on the 28° C. sample. b) TEM image of initial 61-nm diameter pore made by FIB in a 500-nm $Si_3N_4$ membrane. c) TEM image of the same sample after $Ar^+$ ion-beam exposure. Energy dispersive analysis of X-rays in the TEM reveals the presence of Si and N in the membrane that has filled the pore, although the precise composition has not been quantified. Because the transmitted ion current is directly proportional to the area of the pore, the instantaneous pore area indicated in all figures was calculated by multiplying the initial pore area (determined by TEM) by the ratio of the instantaneous to initial transmitted ion current. Temperature, 28° C. Flux, 28 $Ar^+$ $s^{-1}$ $nm^{-2}$. Duty cycle, 200 ms/1 s.

A 0.1 μm diameter bowl-shaped cavity was fabricated in a free-standing $Si_3N_4$ membrane supported on a silicon frame, as shown in FIG. 6a. To produce a molecular-scale nanopore, the sample was ion beam sculpted using 3-keV $Ar^+$ ions in the apparatus described above and shown in FIG. 6b. Surprisingly, experiments on this sample at room temperature did not yield the expected result; a nanopore did not open even after excessively long ion beam exposure. The cause for this was discovered by ion beam sculpting a membrane containing a through-hole, rather than a bowl-shaped cavity. As the sample with a through-hole was exposed to an ion beam at room temperature in the apparatus of FIG. 6b, the transmitted ion counting rate clearly decreased with increasing ion beam exposure, as shown in FIG. 7a, suggesting that the hole was closing rather than opening. The incident ion beam was switched off when the counting rate fell to 40 counts $s^{-1}$, as shown in FIG. 7a, inset.

Transmission electron microscope (TEM) images of the hole before and after the ion beam exposure, as shown in FIGS. 7b and 7c, revealed that the hole size had indeed been reduced from about 60 nm to about 1.8 nm by the growth of a thin membrane of a thickness of about 10 nm, as deduced from electron microscopy. With sufficient ion beam exposure in the apparatus of FIG. 6b, the nanopore completely closed, and the ion count correspondingly was found to fall to zero. This experiment led to a discovery that during exposure of a pore to an ion beam, there must be in addition to ion sputter erosion a lateral atomic flow of matter into the pore by mass transport, stimulated by the ion beam. That this is a surface, or near-surface phenomenon is strongly suggested by computer simulations showing that ion beam energy is deposited within less than about 5 nm of the sample surface.

Figure 8:
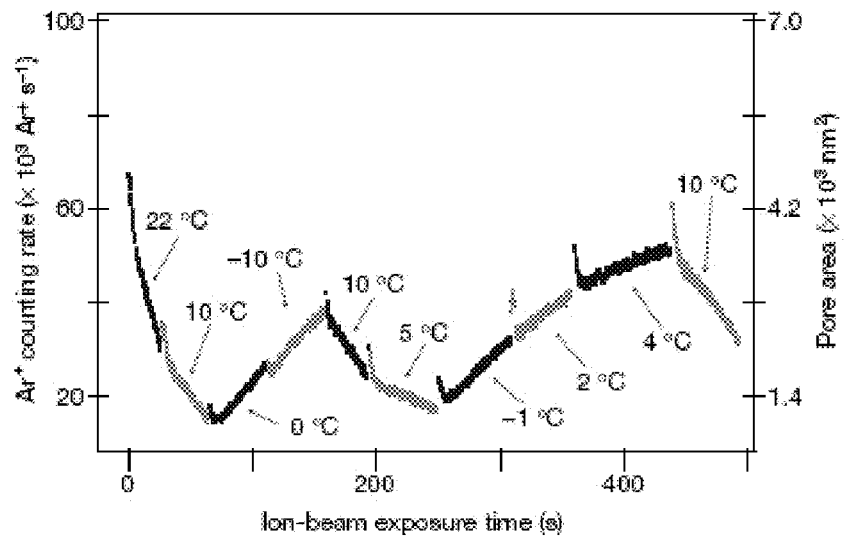
FIG. 8. Temperature dependence of ion-beam sculpting. Successive data sets at different temperatures (shown) are delimited by their alternate black and gray coloration. Flux, 14 $Ar^+$ $s^{-1}$ $nm^{-2}$. Duty cycle, 200 ms/1 s.
Figure 9:
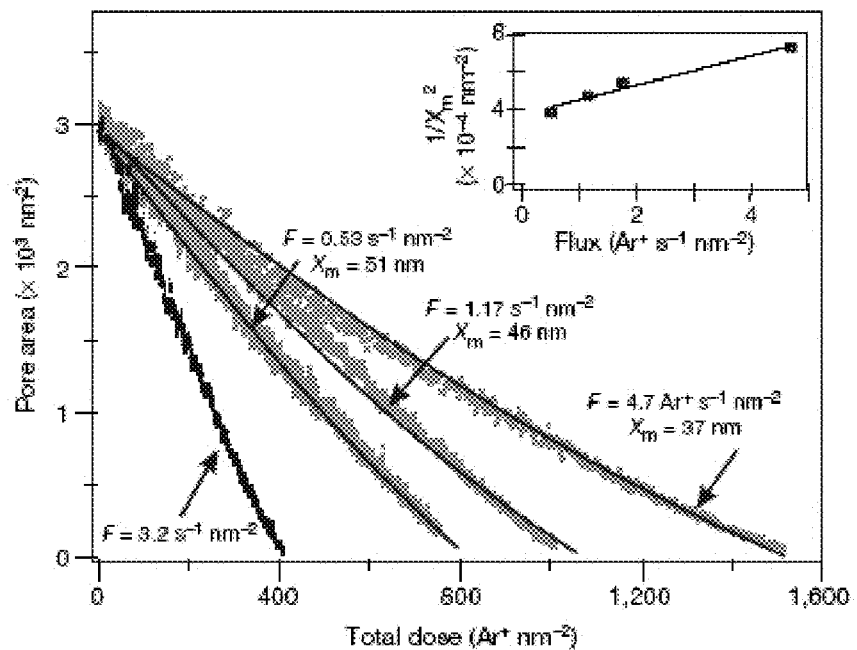
FIG. 9. Flux dependence of ion-beam sculpting. Pore area versus total dose for samples exposed at different instantaneous fluxes, F, to a continuous beam (gray traces), or a pulsed beam (black traces). Duty cycle, 100 ms/1 s. The plotted black curves overlying the gray data points are predicted from the diffusion model under steady-state conditions (see text). The inset plots $1/X_m^2$ versus flux, from which D is extracted. Temperature, 28° C.

It has been found that the flow of matter to a developing or closing nanopore in the apparatus of FIG. 6b is temperature-dependent, as shown in the plot of FIG. 8, where an increasing number of transmitted ions corresponds to an opening (developing) nanopore and a decreasing number of transmitted ions corresponds to a closing nanopore. A transition between pore opening and pore closing is found at about 5° C. under the ion beam conditions of FIG. 8. When pore area is plotted as a function of ion beam dose rather than ion beam exposure time, as shown in FIG. 9, the slope of the data reveals that for continuous beam exposure (the gray trace of FIG. 9) the efficiency of pore closing per incident ion is clearly greater at low fluxes than at high fluxes. The plot of FIG. 9 also shows that a pulsed beam (the black data points) closes pores more efficiently than does a continuous ion beam at the same instantaneous flux.

The invention provides a model of the ion beam sculpting processes and their process parameter dependencies just described, for enabling control of the sculpting processes. Solutions to analytical expressions of the model, as-obtained with appropriate parameter values for a given sculpting process, can be employed in accordance with the invention to produce prespecified nanoscale features in a precise, predictable manner, and in open-loop fashion, i.e., without the need for closed loop ion counting rate feedback control like that employed in the system of FIG. 6b. As explained in detail below, the invention provides a recognition that the sputtering and mass transport phenomena discussed above compete during an ion beam sculpting process. The control methodology of the invention provides the ability to control these phenomena such that one process can dominate over the other in a manner that produces a desired nanoscale feature or geometry.

The parameters employed by the analytical model expressions generally depend on the properties of the material being ion beam sculpted, e.g., the specific material and material defects and doping impurities, as well the local environment around the sculpting process, the temperature of the material, the incident ion species, ion flux, and ion energy, and other parameters that characterize the incident ion beam. It is recognized in accordance with the invention that the process parameters therefore are to be adjusted based on a particular ion beam sculpting application to achieve desired process results, in the manner described below. For example, it is understood that the charge state of the ion beam can impact ion beam sculpting parameters. Positive, neutral, or negative ions can be employed in accordance with the invention to produce a desired charge state between adatoms, described below, that are produced during the sculpting process. Similarly, it is understood that the ambient gas of the sculpting process can impact sculpting parameters. Chemical reactivity of gas species can be catalyzed by the ion beam, resulting in removal or addition of surface adatoms and/or creation or elimination of surface defect traps.

For clarity, the following discussion is directed to a process model based specifically on ion beam sculpting of a nanopore. As explained in detail below, however, the invention is not limited to such. The analytical process model expressions provided by the invention can be adjusted to control formation of a wide range of geometries, e.g., slits or irregularly-shaped holes, trenches, or other geometry, or features such as lithographic mask features, ion beam doping profiles accompanied by mass transport, or buried layer profiles. There is no fundamental geometric symmetry or pattern to which the process control model is limited. Whatever geometry or feature is being formed, it is the nanoscale control of that geometry by the process of the invention that is universally applicable.

As explained above, the model employed by the invention for use in controlling ion beam sculpting is based on a recognition that distinct processes are likely to compete during the sculpting. Considering ion beam sculpting involving a nanopore, a first such process tends to open the pore and is understood to likely be driven by ion beam-sputter erosion of a pore edge. This erosion process is understood to be dominant at low temperatures and high ion beam fluxes. Established sputtering phenomenology can be employed for most applications to account for and control sculpting processes that are dominated by sputtering in this regime.

A second, competing process tends to cause motion of matter, i.e., mass transport, and can operate to a degree necessary for closing the pore. Without being bound to theory, it is understood that more than one view can explain this phenomenon. A first theory understood in accordance with the invention takes the view that a very thin, e.g., about 5 nm-thick, stressed viscous surface layer may be created by the energy and matter deposited on a material surface by an ion beam. An enhanced collective motion, driven by a reduced viscosity and/or enhanced stress owing to implantation effects or surface tension, may cause the layer to relax, whereby material is transported across a surface.

Figure 10:
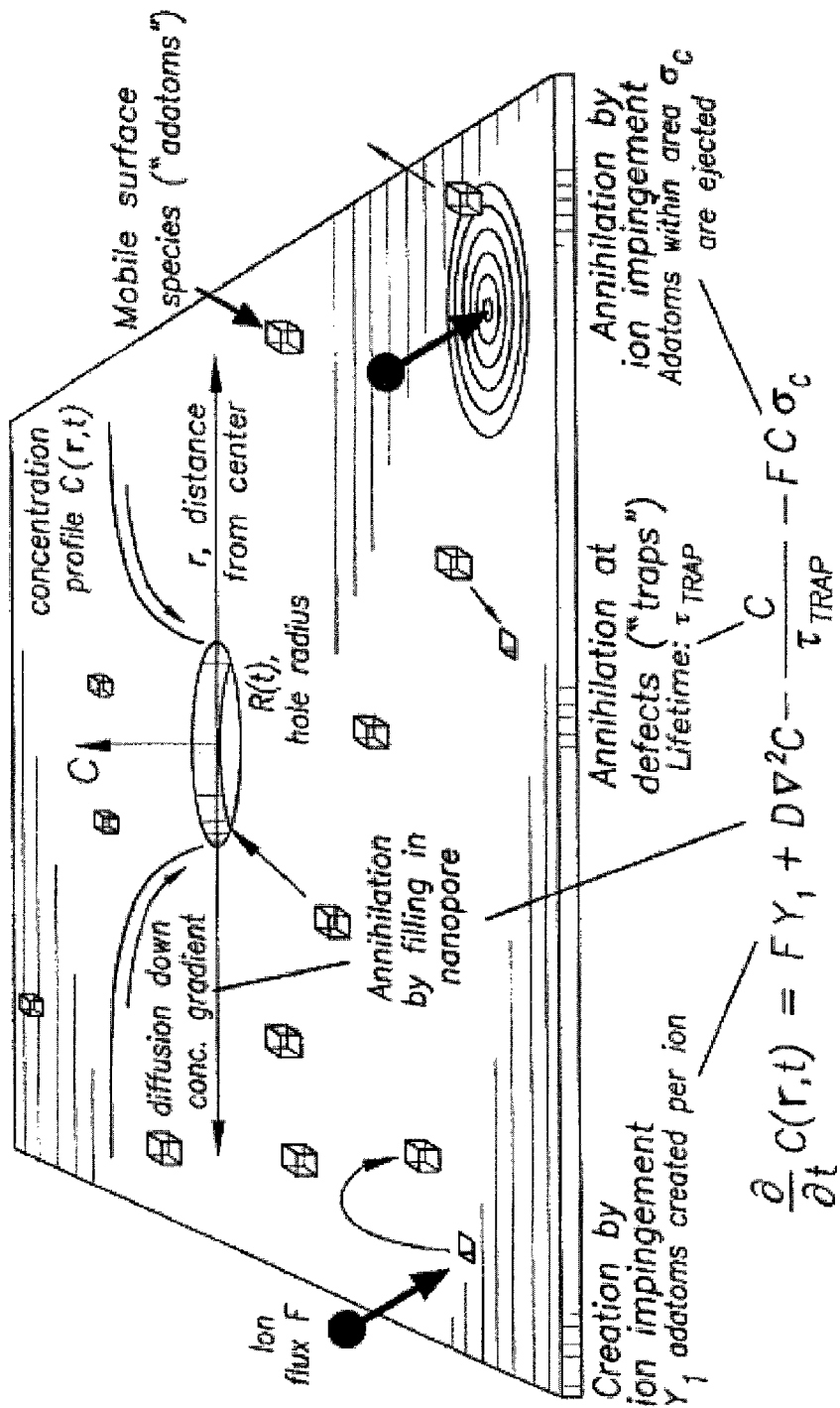
FIG. 10. Schematic view of a solid state structure surface undergoing a material transport and ion sculpting process, identifying physical mechanisms corresponding to various terms of an ion sculpting model provided by the invention.
Figure 11:
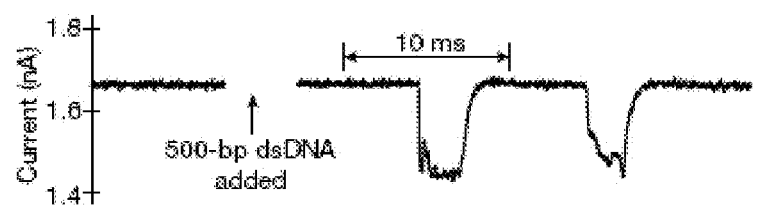
FIG. 11. Molecular events in a nanopore detector. A $Si_3N_4$ membrane with a 5-nm pore separated two compartments filled with saline solution (1M KCl, 10 mM Tris-HCl, 1 mM EDTA, pH 8.0). Initially, with only the saline solution in the compartments, a 120-mV bias between AgCl electrodes in each compartment resulted in a constant ionic current of 1.66 nA through the nanopore. This was consistent with the known conductivity of the ionic solution, assuming a pore length of around 10 nm. After adding double-stranded DNA, 500 base pairs long, to the negatively biased compartment, and allowing time for diffusion, intermittent current blockades (two are illustrated) were observed. $Si_3N_4$ membranes with holes of about 100 nm in diameter that were completely closed by ion beam sculpting produced 20 GΩ seals.

Although this "reduced viscosity" model has merit, in accordance with the invention a preferred ion beam sculpting control model reflects a process theory in which incident ions create as well as annihilate excess, independent, and mobile species such as adatoms, ad-dimers, ad-molecules, molecular clusters, and surface vacancies that are present at the surface of a material exposed to an ion beam. For basic applications, it is understood to be reasonable to assume a single mobile species which, for simplicity, will here be called an "adatom." The changing concentration of surface adatoms, $C(r,t)$, is modeled in accordance with the invention as a function of distance, $r$, the radial coordinate, and time, $t$, as being governed by a two dimensional diffusion equation:

$$\frac{\partial}{\partial t} C(r, t) = FY_1 + D\nabla^2 C - \frac{C}{\tau_{trap}} - FC\sigma_c, \quad (M.1)$$

where $C$ is the concentration of adatoms on a two-dimensional surface, $r=(x,y)$ is the radial surface position, $t$ is time, $F$ is the ion flux, $Y_1$ is the number of adatoms created per incident ion, $D$ is the adatom surface diffusivity, $\tau_{trap}$ is the average lifetime of an trap is adatom before thermally-activated adatom annihilation occurs at a surface defect, and $\sigma_c$ is the cross-section for adatom annihilation by incident ions. With this expression, it is found that $\partial C/\partial t$ depends on a generation rate, resulting from the ion flux and number of created adatoms, a transport factor, driving the adatom transport by diffusion, and two annihilation factors, resulting from surface defects and the incident ion beam itself Annihilation of adatoms also occurs at the pore edge as the pore is filled and is treated as a boundary condition for expression M.1. FIG. 10 illustrates these mechanisms captured in the model.

The first and last terms on the r.h.s. of expression M.1 reflect an understanding provided by the invention that each incident ion resets a surface patch of area $\sigma_c$ to an adatom concentration $Y_1/\sigma_c$ that is independent of its previous state. The presence of a nanopore in the material being subjected to an ion flux is represented by adding an adatom sink at the nanopore edge, for a nanopore radius R, and by adding the second term on the r.h.s. to model long-range diffusion to the pore edge. Adatoms annihilated at the nanopore boundary are turned into new, stable matter at the boundary.

The magnitudes of the parameters $Y_1$, $D$, $\tau_{trap}$, and $\sigma_c$ can be estimated for a given ion beam sculpting application from experience with suitable materials and can be determined by independent experiments, e.g., a matrix of pore-closing experiments, preferably including both steady state and transient conditions. It is recognized in accordance with the invention that the values of these parameters can be manipulated by adjusting not only temperature, ion beam flux, and ion beam energy, but also by adjusting the ambient gas species and pressure, ion species, material properties, e.g., concentrations of trace impurities on the material surface, and material defects and impurity doping. The parameters are therefore treated here as being adjustable to enable precise control of the ion beam sculpting process for a given application.

By comparison with the r.h.s. third term of expression M.1, the average lifetime before ion impingement-induced adatom annihilation is $\tau_{ion}=1/(F\sigma_c)$. The effective surface lifetime $\tau$ in the presence of both annihilation mechanisms is then given as:

$$\frac{1}{\tau} = \frac{1}{\tau_{trap}} + F\sigma_c \qquad (M.2)$$

It is understood that under some circumstances, one of the final r.h.s. two terms of expression M.1 will be insignificant compared to the other, but this may not necessarily always be the case, and is not required for the analysis of the invention. An additional annihilation mechanism, adatom annihilation by joining with other adatoms and precipitating into islands, is not represented in expression M.1 for simplicity so that this partial differential equation is linear, rather than nonlinear, for ease of solution. It is understood, however, that applications for which this annihilation channel cannot be neglected are more precisely modeled with the addition of another term to the r.h.s. of expression M.1 that would be proportional to $-C^n\tau_{island}$, where n is the number of adatoms in the critical island (the island that's just big enough to be more likely to grow than to shrink), and $\tau_{island}$ is a characteristic time constant for island formation. Thermal generation of adatoms, thermal desorption into the vacuum, and deposition from the vapor have also been neglected but can be readily incorporated when necessary for a given application.

Expression M.1 expresses an understanding that far from a nanopore, steady ion irradiation creates a spatially uniform adatom concentration $C_{SS}=FY_1\tau$. The pore boundary, or nanopore edge, is taken to be a "perfect sink" for adatoms, which are there transformed to a thin layer of accumulating matter that accounts for pore closure. If the nanopore edge is taken as a sink for adatoms then the adatom supersaturation drops as the nanopore edge is approached. Expression M.1 implies that the normalized difference, n(r,t), between $C_{SS}$ and C(r,t), given as $n(r,t) \equiv (C_{SS}-C(r,t))/C_{SS}$, obeys a diffusion equation as:

$$\frac{\partial n(r,t)}{\partial t} = D\nabla^2 n - \frac{n}{\tau} \qquad (M.3)$$

The assumption that the pore boundary is a "perfect sink" for adatoms implies that the adatom concentration, C, vanishes at the pore boundary (of radius R). This is the simplest boundary condition that accounts for a net accumulation of adatoms at the pore, and thus for closure. It is recognized in accordance with the invention, however, that because of its interaction with the ion beam, the pore boundary could be a net source of surface vacancies and still produce this pore-closing effect if vacancies, rather than adatoms, dominate surface transport. The invention is therefore not limited to an adatom "perfect sink" boundary condition. An alternative boundary treatment contemplated by the invention employs a surface accommodation velocity to describe a partial sink for adatoms at the pore boundary, in a manner analogous to surface recombination velocity factors employed in semiconductor modeling of charge carriers interacting with surfaces.

Solutions for the spatial adatom concentration profile predicted by the above model, under a quasi-stationary approximation in which the left-hand side of expression M.1 is set to zero, which is justified when the adatom concentration profile adjusts rapidly to changes in R, yield a spatially uniform steady-state adatom supersaturation far from the pore, decaying over a characteristic distance $X_m$ to zero at the nanopore edge.

Because adatoms are being removed everywhere on the surface of a material exposed to an ion beam, as well as being created by the ion beam, adatoms created within a distance $X_m$ of the pore edge are more likely to diffuse to and close the pore than be annihilated by incident ions; the opposite is true of adatoms created farther away. $X_m$ therefore decreases with increasing flux. Obtaining $Y_p$, the effective cross section for sputter-erosion from the pore edge, from relevant data obtained at low temperature, where diffusion is expected to be insignificant, and taking $Y_1$, the number of adatoms created per incident ion, to be of order unity, then for a material thickness of 10 nm, the model yields the solid curves in FIG. 9 for each incident flux given, at a temperature of about 28° C., a temperature experimentally verified to cause pores to close. From this data, a value of D of about $10^3$ nm$^2$s$^{-1}$ is extracted, using a linear fit, with $\sigma$ of about 0.1 nm$^2$ as a reasonable estimate. The model therefore predicts that the maximum distance, $X_m$, from which adatoms are likely to diffuse to and close a pore is linearly proportional to the adatom diffusivity, the trap lifetime, the ion beam flux, and the cross section for adatom annihilation, as:

$$\frac{1}{X_m^2} = \frac{1}{D\tau_{trap}} + \frac{\sigma}{D}F \qquad (M.4)$$

and a linear relation is indeed observed (see inset to FIG. 9). $X_m$ thus is found to represent a characteristic distance from the pore edge within which adatoms are more likely to reach the pore than be annihilated by traps or ion beam flux erosion. Adatoms beyond $X_m$ are more likely to be annihilated before they reach the pore.

As the ion beam flux is increased, the number of adatoms is increased, but the distance from which adatoms can diffuse to and close a pore is reduced. As the average lifetime of an adatom, due to surface defects, is increased, the maximum adatom diffusion distance also increases. As the temperature is increased, the diffusivity, and correspondingly, the maximum adatom diffusion distance, is increased. With the analytical understanding of these relationships provided by the invention, this model enables an ability to prescribe a minimum distance, $X_m$, of material that must be provided around a starting nanopore to provide sufficient material for closing of the nanopore to a desired final radius R under given processing conditions, and enables adjustment of processing conditions to accommodate a given maximum diffusion distance $X_m$.

The adatom flux, or current, j, at any location r is given by $$j(r) = -D\partial C/\partial r \qquad (M.5)$$

with r the radial coordinate, and the concentration gradient evaluated at the edge of the nanopore (r=R) providing the adatom flux j(R) into the nanopore. Additionally, scraping of material off the edge of the nanopore, tending to open the pore, is accounted for by a characteristic cross section for sputter-erosion from the pore edge.

If each adatom reaching the nanopore fills the pore by a volume Q, thereby reducing the extent of the pore, then the nanopore closing rate is predicted by a volume balance given as:

$$\frac{d}{dt}(\pi R^2 H) = 2\pi R\Omega(-j(R) + FY_p) \quad \text{(M.6)}$$

where $Y_p$ is an effective cross section for sputter-erosion from the pore edge, H is the thickness of the film that is formed by filling in the nanopore, and $\Omega$ is the atomic volume. Substituting expression M.5 for the adatom current j(R) results in $$\frac{d}{dt}(\pi R^2) = -\frac{2\pi\Omega RF}{H}\left(Y_1 X_m \frac{K_1\left(\frac{R}{X_m}\right)}{K_0\left(\frac{R}{X_m}\right)} - Y_p\right) \quad \text{(M.7)}$$

where $K_0$ and $K_1$ are modified Bessel functions of the second kind.

This expression enables ion beam sculpting control, for a given set of process parameters characteristic of an ion beam environment, to produce a nanopore of a desired radius R. For example, it is found from this model that pore closing is enhanced with increasing temperature. This can be accounted for by a thermally activated adatom diffusion coefficient.

In accordance with the control method of the invention, expression M.7 can be employed to specify $R_{max}$, the radius of the largest pore that can be closed under any particular set of processing conditions. $R_{max}$ increases with increasing temperature and with decreasing flux. At a sufficiently high temperature and sufficiently low flux, $R_{max}$ becomes infinite, a scenario that determines the conditions under which an open pore can be closed. The radius $R_{max}$ is $$Y_1 X_m \frac{K_1\left(\frac{R}{X_m}\right)}{K_0\left(\frac{R}{X_m}\right)} - Y = 0 \quad \text{(M.8)}$$

With $X_m$, $Y_1$, and $Y_p$ provided as constants, the ratio of $$\frac{K_1\left(\frac{R}{X_m}\right)}{K_0\left(\frac{R}{X_m}\right)}$$

gets smaller with increasing R, so that at $R=R_{max}$ and above, the pore can no longer close. Analysis of this expression thereby enables adjustment of processing conditions to produce a desired $R_{max}$.

It has been observed empirically that the thickness, H, of a growing membrane or film produced as a nanopore is closed depends on the rate of closing, $d(\pi R^2)/dt$, where R is the radius of the nanopore. Higher pore closing rates result in thinner films than lower pore closing rates. In addition, higher ion beam energies result in thicker films than lower ion beam energies. Based on the expressions given above, the invention provides the ability to prescribe a film thickness by selecting ion beam sculpting process conditions that result in a corresponding pore closing rate and ion beam energy.

As explained above, it is understood in general in accordance with the invention that different regions of the perimeter of an arbitrarily-shaped aperture will also open and close according to expressions M.1 through M.3. In addition, expressions M.4 through M.8 can be generalized in an obvious manner to remove the cylindrical symmetry which is assumed in the example given here, to enable modeling and process control of arbitrarily-shaped features. The invention is therefore not limited to a particular feature geometry.

Time dependent solutions of the adatom diffusion model are employed in accordance with the invention to describe a sculpting process employing a pulsed ion beam having a selected duty cycle. In order to model conditions when the incident ion beam is turned off, a steady state condition is assumed. That is, the ion beam flux is set to F=0, and the initial concentration of the adatoms on the surface is given, for the nanopore example above, as:

$$C(r, t=0) = C_{SS}\left[1 - \frac{K_0\left(\frac{r}{X_m}\right)}{K_0\left(\frac{R}{X_m}\right)}\right] \quad \text{(M.9)}$$

where $C_{SS}$, is the steady state adatom concentration far from the pore; so that expression M.1 becomes $$\frac{\partial}{\partial t}C(r, t) = D\nabla^2 C - \frac{C}{\tau_{trap}} \quad \text{(M.10)}$$

Assuming as boundary conditions for the adatom concentration, C:

$$C(R, t) = 0 \quad \text{(M.11)}$$

$$C(b = NX_m, t) = C_{SS}e^{\frac{t}{\tau_{trap}}}$$

where b is an outer boundary condition, far from the pore edge, i.e., N>>1. In practical calculations, N=5 was found to be "big enough", but it is recognized that for some applications, a larger value of N may be required for increased accuracy.

Solutions to expression M.10 provide time dependent solutions of the adatom concentration on the surface of the sample after the beam is off, as:

$$C^{eff}(r, t) = C_{SS}\left[\frac{\ln\left(\frac{r}{R}\right)}{\ln(b/R)} + \sum_{n=1}^{\infty} A_n U_0(\alpha_n r)e^{-\alpha_n^2 Dt}\right]e^{\frac{t}{\tau_{trap}}} \quad \text{(M.12)}$$

where $$A_n = \frac{\pi^2 \alpha_n^2}{2} \frac{J_0^2(\alpha_n R)}{J_0^2(\alpha_n R) - J_0^2(\alpha_n b)}$$

$$\int_R^b r\left[1 - \frac{K_0\left(\frac{r}{X_m}\right)}{K_0\left(\frac{R}{X_m}\right)} - \frac{\ln\left(\frac{r}{R}\right)}{\ln(b/R)}\right]U_0(\alpha_n r)dr$$

where $U_0(\alpha r) = J_0(\alpha r)Y_0(\alpha b) - J_0(\alpha b)Y_0(\alpha r)$ and $U_0(\alpha_n R) = J_0(\alpha_n r)Y_0(\alpha_n b) - J_0(\alpha_n b)Y_0(\alpha_n r) = 0$ provides the roots of $\alpha_n$. $J_0$, and $Y_0$ are Bessel functions of the first kind.

The rate at which the area of a pore decreases when the ion beam is off is given as:

$$\frac{\partial}{\partial t}(\pi R^2) = -\frac{2\pi \Omega RF}{H} D \frac{\partial C^{off}}{\partial r}\bigg|_{r=R} \quad (M.13)$$

When the ion beam is off, adatoms remain on the surface of the material, but the adatom annihilation channel associated with the incident beam flux is no longer present. Thus, after the beam is extinguished, the remaining adatoms can diffuse to the pore periphery from a greatly increased $X_m$. This condition can significantly increase the efficiency per ion for pore closing.

In accordance with the invention, expression M.13 can be employed in combination with expression M.2 to predict and then control the rate of nanopore closing when a pulsed ion beam sculpting process is applied. Specifically, the pulsed ion beam time structure, i.e., the pulse rate and duty cycle, are adjusted in accordance with the invention to achieve control over the sign and rate of change of structural dimensions.

It is recognized in accordance with the invention that as with the conditions when the beam is turned off, there is also a transient solution when the beam is first turned on. This may be important under some conditions, but it is expected that for most applications, the "beam-on" transient is significantly shorter than the "beam-off" transient and therefore can be ignored. If for a given application such is not the case, then the "beam-off" transient analysis given above is preferably extended to the "beam-on" analysis.

The diffusion model employed by the control method of the invention is phenomenological and relies on several idealizations and assumptions necessary to compensate for uncertainty in aspects of many microscopic properties of matter under ion beam exposure. Nevertheless, it is understood by the inventors that studies of pulsed and continuous beam exposures at different temperatures, gas ambients, and material conditions can be employed for a given application in conjunction with the model to permit the determination of materials-specific parameters like $D$, $Y_1$, $\sigma$, and $\tau_{trap}$ for the application to enable prespecified and precise ion beam sculpting of the material in the production of useful nanoscale devices.

Practitioners of ion beam sculpting can use the model provided by the invention in both quantitative and qualitative ways. That is, by knowing the qualitative as well as quantitative nature of the solutions to the analytical model expressions and their dependence on various parameters of the model that are subject to experimental control, these parameters may be adjusted to achieve desired control over the dimensional control of structures for large classes of structures. An example would be a qualitative recognition of the ability to increase the rate of shrinking or even the possibility of shrinking a pore diameter using ion sculpting by increasing the sample temperature or decreasing the incident flux of incident ions, as well as a quantitative recognition of the degree of temperature increase or flux decrease required for a given application. In these examples, practitioners are guided to such action by noting that both of these actions increase the effectiveness of surface diffusion of adatoms over sputtering, by a temperature enhancement of the surface diffusion constant and a reduction in adatom sputtering respectively.

Other qualitative and quantitative uses of the model include correlations between analytical predictions of the model and ancillary empirical observations. An example of this would be the observation that nanopores that are reduced to a desired radius more quickly under the ion beam sculpting process have a smaller aspect ratio, i.e., length to diameter ratio. Although the model at any given stage of its evolution may not contain the details of the process controlling the pore length, it can be used to enhance the pore closing speed and thus improve the aspect ratio.

Thus, as explained above, in accordance with the invention, ion beam sculpting process parameters are adjusted for a given application, based on the model provided by the invention, to enable prescription of nanoscale geometries produced by the sculpting process. These parameters will in general depend on the material being ion sculpted, the environment around the structure during the sculpting process, temperature, and on the incident ion species, energy, and other parameters that characterize the incident ion beam. The incident ion beam can be supplied as atoms, i.e., neutral ions, ions of a controlled charge state, molecules or clusters of incident atoms, or indeed any controlled energy source. It is recognized that differing model parameters will be required for the various energy sources. In addition, the invention contemplates the use of multiple energy sources as well as adjustment of the charge state of the material surface at the start and during the sculpting process.

It is recognized in accordance with the invention that both the surface of a structure being ion sculpted and the ion-induced adatoms on the surface may be highly susceptible to the influence of the environment. By environment is meant a background ambient of a gas like oxygen, hydrogen, sulfur hexafluoride, or other selected gas. As a result the interaction of these gasses with surface atoms or adatoms, the transport of adatoms and or the removal of surface atoms may be greatly modified relative to the case with the absence of such gasses. Consequently the rates and signs of ion sculpting effects will be dramatically modified, and these modifications can be of great utility to the practitioners of the ion beam sculpting process. It is also to be recognized that the state and chemical reactivity of the ambient gas, as well as the excitation state of the surface or charge state of the surface being acted upon, may be influenced by the incident ion beam. Means other than an incident ion beam, such as an electron beam, laser beam, atomic beam, metastable excited atomic beam, mixtures of ion beams, or other energy source, may be used to control the sensitivity of the ion sculpting process to the ambient environment in which it is carried out. Adjustment and control of these various influences are recognized in accordance with the invention to enable flexibility and reproducibility of prespecified and precise ion beam sculpted geometries of a material in the production of useful nanoscale devices.

To demonstrate such a device, a nanopore was sculpted in a $Si_3N_4$ membrane for use as a single-molecule electronic detector of DNA. Proteinaceous nanopores, or channels, have been inserted into lipid bilayers in aqueous solutions where they serve as electronic sensors to identify and characterize single molecules. But proteins in lipid bilayers are labile and the channel diameters they provide cannot easily be adjusted. Robust, solid-state nanopores, fashioned to any desired diameter, could yield new data and understanding of transport in confined spaces, and will make it possible to produce robust single-molecule-sensing devices to characterize molecules of DNA and other biopolymers at unprecedented speeds.

Using electrophysiology techniques, a robust, electrically quiet, 5 nm-diameter pore was tested with double-stranded DNA. After applying a voltage bias that would draw the negatively charged DNA molecules through the nanopore, diminutions of the ionic current were observed, as shown in FIG. 10, reminiscent of the ionic-current blockages observed when single strands of DNA are translocated through the channel formed by α-hemolysin in a lipid bilayer. Because no such blockages were seen during one hour of monitoring before adding DNA, and because the blockages ceased when the voltage bias was reversed, the blockages are attributed to interactions of individual DNA molecules with the nanopore. The duration of these blockages was on the order of milliseconds, and they consistently exhibited current reductions to 88% of the open-pore value. This last value is commensurate with translocation of a rod-like molecule whose cross-sectional area is 3-4 nm$^2$.

The experimental observations, model considerations, and experimental electronic device results all described above indicate that the ion beam-sculpting control method of the invention represents a promising new approach to nanoscale fabrication. Specifically, the invention enables control of sputtering and mass transport processes that compete during an ion beam sculpting process. With feedback control, reproducibility does not depend on precisely matching all conditions and starting dimensions. If, however, such can be achieved, then the control model of the invention enables open loop processing without reliance on ion rate counting or other feedback control. The invention therefore is not limited to features or geometries that can accommodate an ion feedback loop.

The ion beam-sculpting control method of the invention is particularly useful for fabricating a wide variety of nanoscale semiconductor devices, masks, and mechanical features, and is not limited for formation of a pore or a through-hole. Slits, trenches, crosses, doping profiles, resist patterning, buried layer profiles, and other geometries and features can be produced. Similarly, a wide range of materials can be employed, including semiconducting microelectronic materials such as Si, SiO$_2$, Al, conducting materials, e.g., Al, and others. Furthermore, it is recognized that next-generation ion-source arrays and mask technologies, combined with multichannel ion detectors, can be employed to enable highly parallel applications of the nanoscale ion beam sculpting control methods of the invention.

EXAMPLE 1

Evaluation of ds DNA

Methods of the invention will now be discussed relative to DNA analysis. Nanopores employed in this example were fabricated in 25 μm×25 μm free standing silicon nitride membranes supported by 3 mm×3 mm×0.3 mm silicon substrate (100) frames. The 500 nm thick, low stress (~200 MPa tensile) silicon nitride membrane was deposited by low pressure chemical vapor deposition. Photolithography and anisotropic wet chemical etching of silicon were used to create the freestanding SiN membrane. An initial 0.1 μm diameter pore was created at the membrane's center using a focused ion beam (FIB, Micrion 9500) machine. The diameter of this large pore was then decreased to molecular size near one surface of the membrane using feedback controlled ion beam sculpting. The final nanopore resided in a thin, 5-10 nm thick, membrane covering an approximately 0.1 μm diameter cylindrical aperture extending through the thick silicon nitride membrane below.

Nanopore diameters were determined by transmission electron microscopy. Because TEM projects a three dimensional structure on to a two dimensional plane, the image of the inner edge of the pore actually represents the minimum projected diameter of the pore wall at any height and may not correspond to the narrowest physical constriction. Also, because of the inherent inaccuracies of TEM for determining absolute size and the fact that the pores were not perfectly round, all sizes should be taken as estimates to within a nanometer of the actual pore size.

FIG. 1b shows a diagram of the apparatus. The nanopore on the silicon chip separates two chambers filled with buffered salt solution (1M KCl, 10 mM TRIS-HCl, pH 8.0). Presoaking the chip in isopropanol was found to aid wetting the pore. The cis chamber, to which DNA molecules are added, is at the top of the figure and the trans chamber at the bottom. Both chambers are made of PDMS (polydimethylsiloxane) and are equipped with AgCl electrodes across which a voltage bias is applied during experiments. The electrode in the trans chamber is positively biased and connected to current sensing electronics, while the other electrode is connected to signal ground.

Double-stranded (ds) DNA with ~3 kilobase-pairs (kbp) and 10 kbp were used in this work. The 3 kbp DNA was prepared from pUC19 plasmid (New England Biolabs). The plasmid was cleaved at a single site with SmaI restriction enzyme to produce blunt-ended linear double-stranded DNA. The purity and quantity of the recovered DNA following phenol extraction were assessed by agarose gel electrophoresis and UV absorbance. The 10 kbp KBA plasmid was linearized by digestion with the SmaI and purified following agarose gel electrophoresis using the QIAquick gel extraction kit (QIAGEN Inc., Valencia, Calif.). The DNA was concentrated by ethanol precipitation as described by Sambrook, et. al. (Molecular Cloning; a laboratory manual, Cold Spring Harbor) and stored dry at 4° C. Dried DNA was suspended in 10 mM Tris, 1 mM EDTA pH 7.6 (RT) prior to use. Typical concentrations of DNA in the cis chamber were ~10 nM.

Ionic current through the solid-state nanopore was measured and recorded using an Axopatch 200B integrating patch clamp amplifier system (Axon Instrument) in resistive feedback mode. Signals were preprocessed by a 10 kHz low pass filter. Except for the data displayed in FIG. 1c, which is a live recording, all data was acquired in event driven acquisition mode, meaning analog start and stop triggers were used to determine when data was to be recorded.

In an experimental arrangement in accordance with the invention, open pore ionic conduction was established with 120 mV bias across a nanopore. Then DNA was added to the negative cis chamber, and current blockades appeared in the form of isolated transient reductions in current flow through the pore. FIG. 1c shows part of a current trace recorded for 3 kb DNA (~1 μm long) and a 3 nm pore. Each event is the result of a single molecular interaction with the nanopore and is characterized by its time duration $t_d$ and its current blockage, $\Delta I_b$, ~120 pA. The expected current blockage from a single molecule blocking the pore is linearly dependent on the cross-sectional area of the molecule and independent of the area of the pore, although because the blockage current varies inversely with the thickness of the pore, different pores may produce different blockage currents for the same molecule. Occasionally, the baseline level shifted for very long periods of time by a magnitude similar to that belonging to the discrete transient molecular event. This was likely due to a single molecule that became "stuck" in the nanopore.

Figure 2:
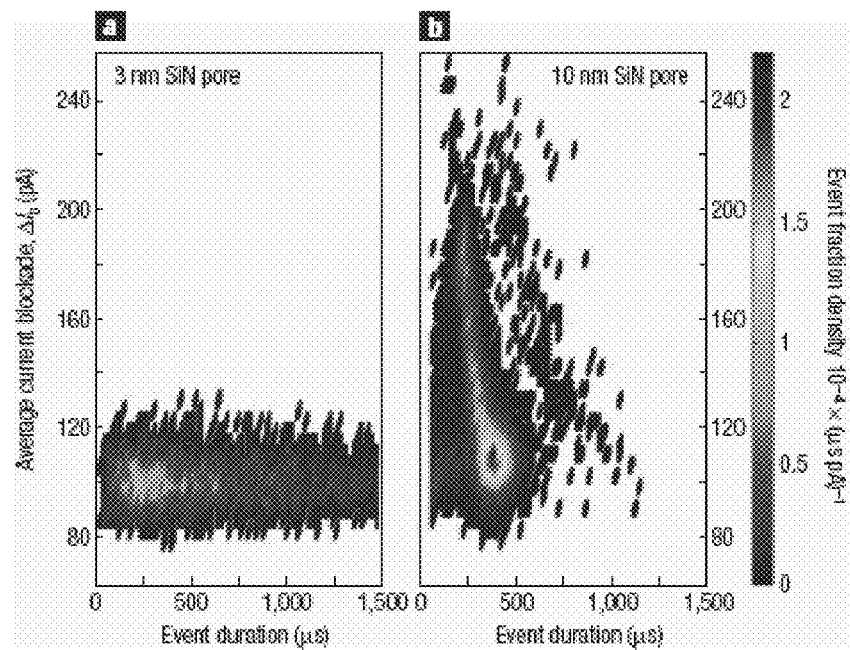
FIG. 2. Distribution of events as a function of $t_d$ and $<\Delta I_b>$ for 10 kbp DNA with a) a 3 nm pore, 2674 events, and b) with a 10 nm pore, 9477 events. The bias voltage was 120 mV. The scale represents event fraction density normalized as a probability distribution so that the integral of the density over all $t_d$ and $<\Delta I_b>$ is equal to 1.

FIG. 2 shows two plots of the density distribution from many transient molecular events over the parameters $\langle \Delta I_b \rangle$ and $t_d$. $\langle \Delta I_b \rangle$ is defined as the average value of a current blockade over $t_d$ (regardless of the signal's shape). FIG. 2a is obtained from experiments using 10 kbp ds DNA with a 3 nm pore and FIG. 2b from experiments with 10 kbp ds DNA and a 10 nm pore. The voltage bias across the pore in both cases was 120 mV. The coding is keyed to the local density of events normalized by the total number of events for each case. Although both distributions peak at $t_d$ ~300-400 μsec the distribution in $t_d$ is quite broad for the 3 nm pore experiment and much sharper for the 10 nm pore experiment. The distribution of events in $<\Delta I_b>$ for the 10 nm pore is much broader than for the 3 nm pore, with larger $<\Delta I_b>$ events showing a definite trend towards having smaller values of $t_d$. FIG. 2b also shows evidence for attractive interactions between different molecules that very occasionally pair up to provide single translocation events for two connected molecules. These appear as a "ghost" structure at twice the expected translocation times. Although very few, these events form a separate cluster clearly seen in the figure. There are too many of these events to be explained as a simple consequence of the Poisson distribution of event arrivals.

Figure 3:
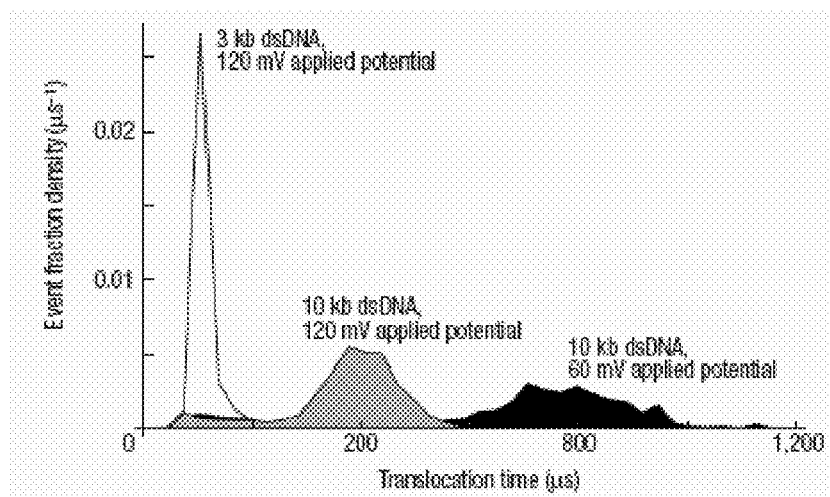
FIG. 3. Plot of the translocation time distribution function for 3 kbp and 10 kbp DNA molecules in a 10 nm nanopore at 120 mV bias, and for 10 kbp DNA at 60 mV bias.
Figure 4:
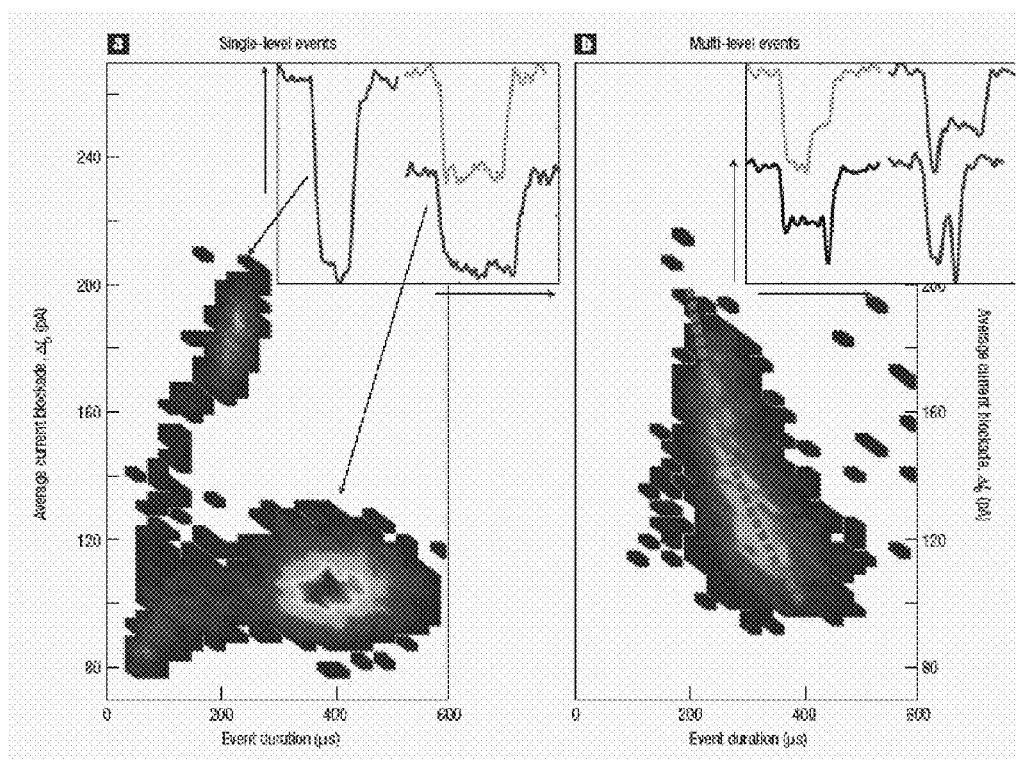
FIG. 4. Density of events over $t_d$ and $<\Delta I_b>$ where plot a) contains simple events characterized by a single blockade level, and plot b) contains the remaining complex events. The inserts show examples of blockade current time traces of events that contribute to the density plots. Isolated regions with only one event in a 20 μsec by 2 pA bin are not displayed in this plot. The scale is the same as in FIG. 2. The dotted line in b) represents the prediction of equation (1) in the text with $t_0$=400 μsec and $<\Delta I_0>$=100 pA.

A visual study of individual events for the 3 nm pore plotted in FIG. 2a shows them all to be simple single level current blockades of the type at the bottom of FIG. 1c (see also inset FIG. 4a). Approximately 60% of the events in 10 nm pore experiments are of this type, but the remainder are more complex (see inset FIG. 4b). Selecting simple single level events from the 10 nm pore data significantly sharpens the distribution in both $<\Delta I_b>$ and $t_d$. In FIG. 3, a histogram is shown of $t_d$ values for simple events in three experiments using 10 nm pores: 3 kbp ds DNA with 120 mV bias, 10 kbp ds DNA with 120 mV bias, and 10 kbp ds DNA with 60 mV bias. The 10 kbp DNA is seen to take slightly more than 3 times longer to negotiate the pore than the 3 kbp DNA at the same bias. Reducing the bias by a factor of two approximately doubles the translocation time. These observations provide strong evidence that each simple single level event corresponds to a DNA molecule translocating in single file order through the nanopore under the influence of electrophoretic forces. The structure of the more complex signals confirms this interpretation, as discussed herein.

FIG. 4a shows the density plot of the simple translocation events for 10 kbp DNA passing through the 10 nm pore. The main cluster of events is narrowly distributed in both $<\Delta I_b>$ and $t_d$. The second cluster is discussed below, but note its mean $<\Delta I_b>$ is twice that of the main cluster, while its mean $t_d$ is half Characteristic time recordings of events from these two regions of the density plot are shown in the inset.

FIG. 4b shows a density plot for more complex "multi-level" events that remain after the simple ones are subtracted. Examples of event time recordings in this group are shown in the inset. They look like simple events on which additional blockade structure has been superimposed. For ~85% of the complex events the additional structure appears at the front of the event, ~5% at the rear, 1-2% at both the front and rear, and 5% in the middle. Half of the events with structure in the middle have $t_d$>400 μsec. (More complex structures are also observed in longer $t_d$ events.)

It is recognized in accordance with the invention that these additional features are attributable to DNA molecules that are folded on themselves as they pass through the pore. As overlapping folded parts of a molecule pass through the pore they enhance the current blockade during that part of the event. If the instantaneous current blockade is proportional to the number of strands of the same molecule in the pore (i.e., one or two), one calculates that the average current blockade for the event will be inversely proportional to the translocation time $t_d$, $$<\Delta I_b> = <\Delta I_0> t_0/t_d \tag{1}$$

where $<\Delta I_0>$ and $t_0$ are the mean current blockage and translocation time of a simple event. This simple model, plotted as the dotted line in FIG. 4b, shows excellent agreement with the data. The smaller cluster in FIG. 4a is thus interpreted as due to molecules that are folded nearly in the middle of the strand. Residual closed circle plasmid DNA in the sample preparation could presumably contribute to this peak.

Figure 5:
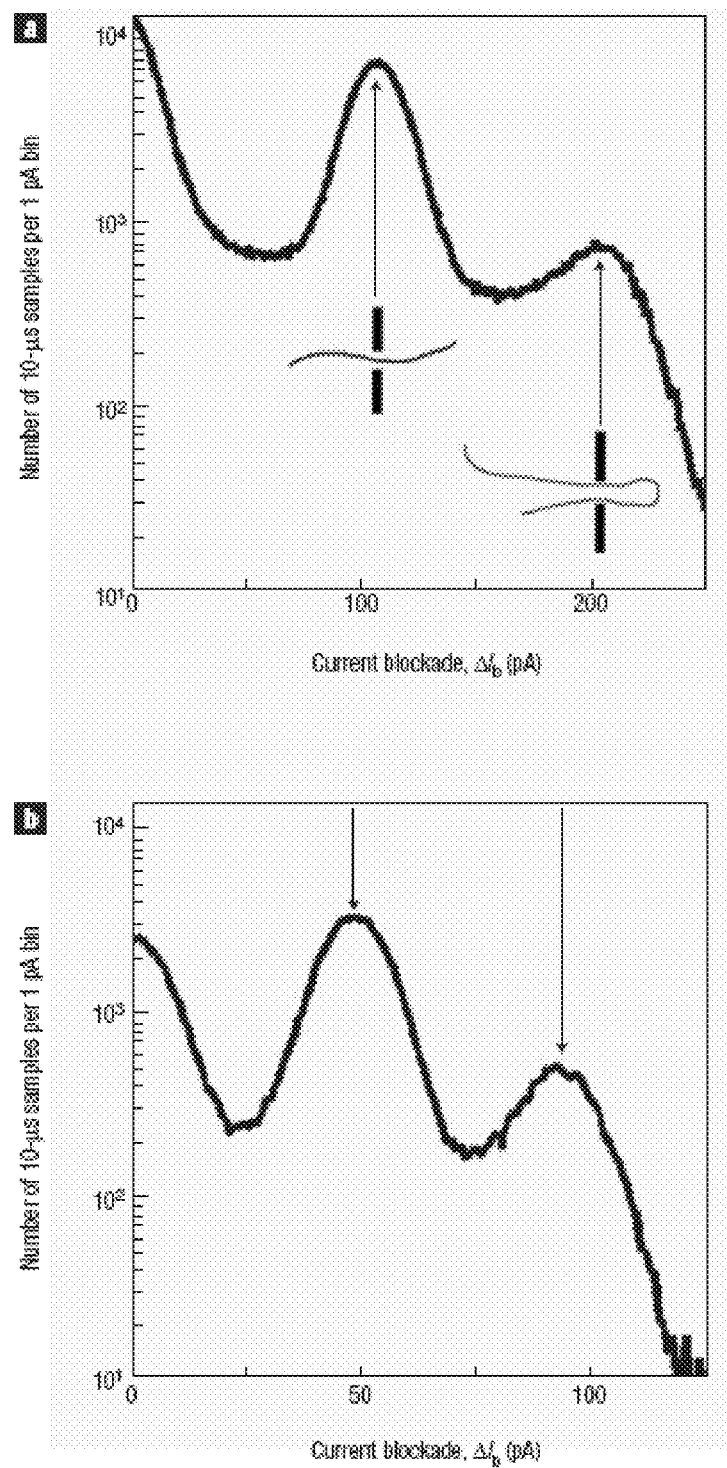
FIGS. 5a-5b. Plots of the instantaneous time distribution of blockade current $\Delta I_b$ over all events. Current is sampled in a 10 microsecond time window. The quantized blockade currents corresponding to 0, 1, and 2 strands in the pore are clearly seen for 10 kbp DNA data from a 10 nm pore for both (a) 120 mV bias and (b) 60 mV bias.

More confirmation that complex nanopore signals correspond to events where folded DNA molecules translocate through the pore is provided by a study of the distribution of instantaneous blockade current magnitudes over all events. Assuming the instantaneous magnitude of the blocked current is in proportion to the instantaneous number of strands of ds DNA in the nanopore, it is expected that the distribution of blocked currents taken over many events, in time samples much smaller than an event duration, shows a quantization of local instantaneous $\Delta I_b$ values corresponding to 0,1,2, . . . strands of the folded molecule in the pore at any particular time. A histogram of these sampled values of $\Delta I_b$ for 10 μsec samples over ~9500 events (including 200 μsec before and after each event) is shown in FIG. 5a for the 10 kb, 120 mV data and in FIG. 5b for the 10 kb, 60 mV data. The expected quantization of sampled $\Delta I_b$ values is clearly seen corresponding to zero, one and two molecule strands occupying the nanopore (note the log scale). Experiments with 50 kbp DNA and a 15-20 nm pore (data not shown) also show three level blockades.

The average speed of polymer DNA molecules translocating through 120 mV biased 10 nm pores is ~1 cm/sec. A quantitative understanding of this result can involve many complex issues like hydrodynamic interactions and screenings, electro-osmotic flow in and near the pore, and non-equilibrium statistical considerations. A simple combination of likely relevant parameters, derived by equating the electric force on the charged polymer in the pore to a viscous drag on an effective sphere of radius a on either side of the pore, gives an average translocation speed of $$v = C \frac{\sigma V_{bias}}{(2a)(6\pi\eta)} \tag{2}$$

where σ is the linear charge density on the molecule, η the viscosity of the solution, $V_{bias}$ the pore voltage bias, and C is a factor of order unity accounting for the complex issues mentioned above. Setting α to the persistence length of DNA (which implies statistical loss of effective drag force beyond that distance) and assuming a charge of e/3 per phosphate, it is found that C~½ brings equation (2) in line with the experimental observations. This crude result suggests that understanding translocation speed may well require only a mesoscopic fluid dynamical description without the need for invoking strong chemically specific complex interactions between molecule and pore. The agreement also strengthens the notion that the observed signals correspond to molecular translocations.

The observed structured events provide additional compelling evidence in favor of translocation. The quantization of current blockage levels shows that molecules must be completely threading the pore (if molecules were partially blocking the pore, one would expect a continuous range of blockade currents corresponding to different degrees of pore occlusion). The large electric force (8 kT/nm for 120 mV bias) on a ds DNA molecule in the pore ensures that a molecule that fully enters the pore will translocate. Finally, the fact that deeper blockages correspond to shorter events and the good agreement of the data with equation (1) are consistent only with folded molecules translocating the pore.

Thus, the technique and apparatus provided by the invention enables the detection of the presence of polymer, e.g., DNA, molecules as well as the detection and observation of the translocation of individual molecules through a solid state nanopore.

The majority of leading edge folds might be expected to result from a molecule initially encountering the pore at some distance from its end with the electrophoretic force from the pore forcing a fold as the translocation starts. Simple energetic considerations using the charge on the molecule and its elastic constant show that this is quite possible for the electric fields and pore sizes employed experimentally. This does not explain the trailing edge folds which are here ascribed to the pre-existing state of the molecule (before translocation).

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are in the claims.

What is claimed is:

1. A method for determining the conformation of a nucleic acid, said method comprising the steps of:
   (a) providing an apparatus comprising:
   (i) a solid state membrane having a nanopore sized to allow passage of said nucleic acid in said conformation;
   (ii) first and second fluid reservoirs separated by said membrane and fluidically connected via said nanopore; and
   (iii) a detector capable of detecting time-dependent changes in transport properties of said nanopore;
   (b) placing said nucleic acid in said first reservoir;
   (c) causing said nucleic acid to traverse said nanopore; and
   (d) measuring said transport properties of said nanopore over time to determine the conformation of said nucleic acid, wherein said conformation comprises structure formed from binding of a chemical species to said nucleic acid.

2. The method of claim 1, wherein said nucleic acid is single stranded.

3. The method of claim 2, wherein said nucleic acid is DNA.

4. The method of claim 2, wherein said nucleic acid is RNA.

5. The method of claim 1, wherein said transverse dimension of said nanopore is at least 4 nm.

6. The method of claim 1, wherein said transverse dimension of said nanopore is at least 10 nm.

7. The method of claim 1, wherein said transverse dimension of said nanopore is at least 15 nm.

8. The method of claim 1, wherein a longitudinal dimension of said nanopore is between 1-1000 nm.

9. The method of claim 1, wherein changes in said transport properties over time are indicative of whether said chemical species is bound to or dissociated from said nucleic acid.

10. The method of claim 1, further comprising determining the location of binding of said chemical species to said nucleic acid.

11. The method of claim 1, wherein said chemical species comprises a nucleic acid probe or nucleic acid primer.

12. A method for evaluating the effects of an intervention on the conformation of a nucleic acid, said method comprising the steps of:
   (a) providing an apparatus comprising:
   (i) a solid state membrane having a nanopore sized to allow passage of said nucleic acid in said conformation;
   (ii) first and second fluid reservoirs separated by said membrane and fluidically connected via said nanopore; and
   (iii) a detector capable of detecting time-dependent changes in transport properties of said nanopore;
   (b) providing transport properties of said nanopore over time of said nucleic acid in the absence of said intervention, wherein changes in said transport properties over time are indicative of the conformation of said nucleic acid in the absence of said intervention;
   (c) placing said nucleic acid in said first reservoir;
   (d) applying said intervention prior to step (e);
   (e) causing said nucleic acid to traverse said nanopore;
   (f) measuring said transport properties of said nanopore over time, wherein changes in said transport properties over time are indicative of the conformation of said nucleic acid in the presence of said intervention; and
   (g) comparing the transport properties of said nanopore over time from steps (b) and (f) to determine the effect of said intervention on the conformation of said nucleic acid, wherein said intervention comprises a chemical species.

13. The method of claim 12, wherein said chemical species is a candidate binding compound, a denaturant, a nucleic acid probe, or a nucleic acid primer.

14. The method of claim 12, wherein said nucleic acid is single stranded.

15. The method of claim 14, wherein said nucleic acid is DNA.

16. The method of claim 14, wherein said nucleic acid is RNA.

17. The method of claim 12, wherein said transverse dimension of said nanopore is at least 4 nm.

18. The method of claim 12, wherein said transverse dimension of said nanopore is at least 10 nm.

19. The method of claim 12, wherein said transverse dimension of said nanopore is at least 15 nm.

20. The method of claim 12, wherein a longitudinal dimension of said nanopore is between 1-1000 nm.

21. The method of claim 12, furthering comprises repeating steps (d)-(f), wherein the intervention in the repetition of step (d) is changed in type or extent.

22. The method of claim 1, wherein said nucleic acid is double stranded.

23. The method of claim 12, wherein said nucleic acid is double stranded.

24. A method for determining the location of binding of a chemical species to a nucleic acid, said method comprising the steps of:
   (a) providing an apparatus comprising:
   (i) a solid state membrane having a nanopore sized to allow passage of said nucleic acid bound to said chemical species;
   (ii) first and second fluid reservoirs separated by said membrane and fluidically connected via said nanopore; and
   (iii) a detector capable of detecting time-dependent changes in transport properties of said nanopore;

(b) causing said nucleic acid bound to said chemical species to traverse said nanopore; and (c) measuring said transport properties of said nanopore over time to determine the location of binding of said chemical species to said nucleic acid.

25. The method of claim 24, wherein said nucleic acid is single stranded.

26. The method of claim 24, wherein said nucleic acid is double stranded.

27. The method of claim 24, where said chemical species is a probe or primer.

28. The method of claim 24, wherein said apparatus further comprises electrodes disposed adjacent the nanopore.

29. The method of claim 24, wherein said nucleic acid is single stranded, and said chemical species is a probe or primer.

30. The method of claim 24, further comprising determining the chemical makeup of the nucleic acid.

* * * * *